(12) United States Patent
McDevitt et al.

(10) Patent No.: US 7,491,552 B2
(45) Date of Patent: Feb. 17, 2009

(54) FLUID BASED ANALYSIS OF MULTIPLE ANALYTES BY A SENSOR ARRAY

(75) Inventors: John T. McDevitt, Austin, TX (US); Eric V. Anslyn, Austin, TX (US); Jason B. Shear, Austin, TX (US); Dean P. Neikirk, Austin, TX (US)

(73) Assignee: The Board of Regents of The University of Texas System, Austin, TX (US)

( * ) Notice: Subject to any disclaimer, the term of this patent is extended or adjusted under 35 U.S.C. 154(b) by 0 days.

(21) Appl. No.: 11/039,054

(22) Filed: Jan. 20, 2005

(65) Prior Publication Data

US 2005/0164320 A1    Jul. 28, 2005

Related U.S. Application Data

(62) Division of application No. 09/287,248, filed on Apr. 7, 1999, now Pat. No. 6,908,770.

(60) Provisional application No. 60/093,111, filed on Jul. 16, 1998.

(51) Int. Cl.
*G01N 33/543* (2006.01)

(52) U.S. Cl. .................. 436/518; 436/523; 436/524; 422/68.1; 422/81; 422/82.01; 422/82.07; 435/287.1; 435/287.2; 435/288.4; 435/288.7; 435/7.1

(58) Field of Classification Search .................. 436/518, 436/164, 501, 523, 524, 800, 805; 422/68.1, 422/81, 82.01, 243, 82.07; 435/287.1, 287.2, 435/288.4, 288.7; 356/38, 45, 73, 311, 335
See application file for complete search history.

(56) References Cited

U.S. PATENT DOCUMENTS

| 3,696,932 | A | 10/1972 | Rosenberg |
| 3,701,433 | A | 10/1972 | Krakauer et al. |

(Continued)

FOREIGN PATENT DOCUMENTS

DE    19736641    3/1999

(Continued)

OTHER PUBLICATIONS

Lavigne, John. Solution-Based Analysis of Multiple Analytes by a sensor array: Toward the Development of an "Electronic Tongue". Jul. 1998. Journal of the Americn Chemical Society, vol. 120, pp. 6429-6430.*

(Continued)

*Primary Examiner*—Long V Le
*Assistant Examiner*—Melanie J. Yu
(74) *Attorney, Agent, or Firm*—Fulbright & Jaworski LLP

(57) ABSTRACT

A system for the rapid characterization of multi-analyte fluids, in one embodiment, includes a light source, a sensor array, and a detector. The sensor array is formed from a supporting member into which a plurality of cavities may be formed. A series of chemically sensitive particles are, in one embodiment positioned within the cavities. The particles may be configured to produce a signal when a receptor coupled to the particle interacts with the analyte. Using pattern recognition techniques, the analytes within a multi-analyte fluid may be characterized.

13 Claims, 17 Drawing Sheets

U.S. PATENT DOCUMENTS

| | | |
|---|---|---|
| 3,709,868 A | 1/1973 | Spector |
| 3,843,696 A | 10/1974 | Wagner et al. |
| 3,856,469 A | 12/1974 | Schneider et al. |
| 3,876,504 A | 4/1975 | Koffler |
| 3,954,623 A | 5/1976 | Hammer et al. |
| 3,964,974 A | 6/1976 | Banauch et al. |
| 4,036,946 A | 7/1977 | Kleinerman |
| 4,050,898 A | 9/1977 | Goffe et al. |
| 4,069,017 A | 1/1978 | Wu et al. |
| 4,115,277 A | 9/1978 | Swank |
| 4,189,382 A | 2/1980 | Zine, Jr. |
| 4,200,613 A | 4/1980 | Alfrey et al. |
| 4,245,041 A | 1/1981 | Denney |
| 4,246,107 A | 1/1981 | Takenaka et al. |
| 4,294,817 A | 10/1981 | Burgett |
| 4,344,743 A | 8/1982 | Bessman et al. |
| 4,360,611 A | 11/1982 | Wakimoto et al. |
| 4,378,429 A | 3/1983 | Modrovich |
| 4,477,575 A | 10/1984 | Vogel et al. |
| 4,493,815 A | 1/1985 | Fernwood et al. |
| 4,567,149 A | 1/1986 | Sell et al. |
| 4,596,657 A | 6/1986 | Wisdom |
| 4,623,461 A | 11/1986 | Hossom et al. |
| 4,661,445 A | 4/1987 | Saxinger et al. |
| 4,672,028 A | 6/1987 | Olson |
| 4,681,742 A | 7/1987 | Johnson et al. |
| 4,683,195 A | 7/1987 | Mullis et al. |
| 4,683,202 A | 7/1987 | Mullis |
| 4,734,372 A | 3/1988 | Rotman |
| 4,753,776 A | 6/1988 | Hillman et al. |
| 4,777,021 A * | 10/1988 | Wertz et al. .................. 422/101 |
| 4,795,698 A | 1/1989 | Owen et al. |
| 4,810,378 A | 3/1989 | Carmen et al. |
| 4,813,277 A | 3/1989 | Miller et al. |
| 4,828,386 A | 5/1989 | Matkovich et al. |
| 4,855,225 A | 8/1989 | Fung et al. |
| 4,874,499 A | 10/1989 | Smith et al. |
| 4,908,112 A | 3/1990 | Pace |
| 4,925,800 A | 5/1990 | Kovacs |
| 4,938,742 A | 7/1990 | Smits |
| 4,965,188 A | 10/1990 | Mullis et al. |
| 4,988,618 A | 1/1991 | Li et al. |
| 4,997,577 A | 3/1991 | Stewart |
| 5,053,197 A | 10/1991 | Bowen |
| 5,071,076 A | 12/1991 | Chagnon et al. |
| 5,096,807 A | 3/1992 | Leaback |
| 5,108,933 A | 4/1992 | Liberti et al. |
| 5,126,276 A | 6/1992 | Fish et al. |
| 5,130,238 A | 7/1992 | Malek et al. |
| 5,137,031 A | 8/1992 | Guirgui |
| 5,137,833 A | 8/1992 | Russell |
| 5,143,853 A | 9/1992 | Walt |
| 5,147,606 A | 9/1992 | Charlton et al. |
| 5,156,810 A | 10/1992 | Ribi |
| 5,156,972 A | 10/1992 | Issachar |
| 5,162,863 A | 11/1992 | Ito |
| 5,168,044 A | 12/1992 | Joyce et al. |
| 5,182,366 A | 1/1993 | Huebner et al. |
| 5,188,934 A | 2/1993 | Menchen et al. |
| 5,209,904 A | 5/1993 | Forney et al. |
| 5,211,850 A | 5/1993 | Shettigar et al. |
| 5,219,763 A | 6/1993 | Van Hoegaerden |
| 5,223,393 A | 6/1993 | Khanna et al. |
| 5,235,028 A | 8/1993 | Barany et al. |
| 5,240,640 A | 8/1993 | Siiman et al. |
| 5,244,636 A | 9/1993 | Walt et al. |
| 5,244,813 A | 9/1993 | Walt et al. |
| 5,248,742 A * | 9/1993 | McGarry et al. ............ 525/531 |
| 5,250,264 A | 10/1993 | Walt et al. |
| 5,252,294 A | 10/1993 | Kroy et al. |
| 5,252,494 A | 10/1993 | Walt et al. |
| 5,262,127 A | 11/1993 | Wise et al. |
| 5,278,303 A | 1/1994 | Krepinsky et al. |
| 5,288,214 A | 2/1994 | Fukuda et al. |
| 5,296,375 A | 3/1994 | Kricka et al. |
| 5,307,144 A | 4/1994 | Hiroshi et al. |
| 5,366,860 A | 11/1994 | Bergot et al. |
| 5,374,530 A | 12/1994 | Nuzzolo et al. |
| 5,382,512 A * | 1/1995 | Smethers et al. ................ 435/6 |
| 5,385,709 A | 1/1995 | Wise et al. |
| 5,391,272 A | 2/1995 | O'Daly et al. |
| 5,405,784 A | 4/1995 | Van Hoegaerden |
| 5,472,672 A | 12/1995 | Brennan |
| 5,478,751 A * | 12/1995 | Oosta et al. .................. 436/165 |
| 5,480,723 A | 1/1996 | Klainer et al. |
| 5,491,097 A | 2/1996 | Ribi et al. |
| 5,498,392 A * | 3/1996 | Wilding et al. ............. 422/68.1 |
| 5,499,909 A | 3/1996 | Yamada et al. |
| 5,503,985 A | 4/1996 | Cathey et al. |
| 5,512,490 A | 4/1996 | Walt et al. |
| 5,518,887 A | 5/1996 | Parsons et al. |
| 5,541,057 A | 7/1996 | Bogart et al. |
| 5,547,682 A | 8/1996 | Chagnon et al. |
| 5,548,661 A | 8/1996 | Price et al. |
| 5,550,373 A | 8/1996 | Cole et al. |
| 5,563,042 A | 10/1996 | Phillips et al. |
| 5,567,627 A | 10/1996 | Lehnen |
| 5,583,054 A | 12/1996 | Ito et al. |
| 5,587,128 A | 12/1996 | Wilding et al. |
| 5,593,838 A * | 1/1997 | Zanzucchi et al. ............. 435/6 |
| 5,597,531 A | 1/1997 | Libertie et al. |
| 5,611,676 A | 3/1997 | Ooumi et al. |
| 5,616,698 A | 4/1997 | Krepinsky et al. |
| 5,616,790 A | 4/1997 | Arnold et al. |
| 5,631,130 A | 5/1997 | Leckie et al. |
| 5,632,876 A | 5/1997 | Zanzucchi et al. |
| 5,653,939 A | 8/1997 | Hollis et al. |
| 5,654,497 A | 8/1997 | Hoffheins et al. |
| 5,677,196 A | 10/1997 | Herron et al. |
| 5,681,484 A | 10/1997 | Zanzucchi et al. |
| 5,690,763 A * | 11/1997 | Ashmead et al. ............... 156/60 |
| 5,690,807 A | 11/1997 | Clark, Jr. et al. |
| 5,698,089 A | 12/1997 | Lewis et al. |
| 5,698,271 A | 12/1997 | Liberti et al. |
| 5,700,897 A | 12/1997 | Klainer et al. |
| 5,705,018 A | 1/1998 | Hartley |
| 5,707,502 A | 1/1998 | McCaffrey et al. |
| 5,714,122 A | 2/1998 | Bretscher et al. |
| 5,747,349 A | 5/1998 | Van Den Engh et al. |
| 5,748,091 A | 5/1998 | Kim |
| 5,755,942 A | 5/1998 | Zanzucchi et al. |
| 5,756,291 A | 5/1998 | Griffin et al. |
| 5,759,015 A | 6/1998 | Van Lintel et al. |
| 5,770,370 A | 6/1998 | Kumar |
| 5,770,416 A | 6/1998 | Lihme et al. |
| 5,773,307 A | 6/1998 | Colin et al. |
| 5,779,907 A | 7/1998 | Yu |
| 5,788,814 A | 8/1998 | Sun et al. |
| 5,797,898 A | 8/1998 | Santini, Jr. et al. |
| 5,814,524 A | 9/1998 | Walt et al. |
| 5,827,748 A | 10/1998 | Golden |
| 5,834,318 A | 11/1998 | Buettner |
| 5,837,552 A | 11/1998 | Cotton et al. |
| 5,840,256 A | 11/1998 | Demers et al. |
| 5,843,655 A | 12/1998 | McGall |
| 5,843,767 A | 12/1998 | Beattie |
| 5,846,396 A | 12/1998 | Zanzucchi et al. |
| 5,846,708 A | 12/1998 | Hollis et al. |
| 5,854,141 A | 12/1998 | Cronin et al. |
| 5,854,684 A | 12/1998 | Stabile et al. |
| 5,856,174 A | 1/1999 | Lipshutz et al. |
| 5,858,804 A | 1/1999 | Zanzucchi et al. |
| 5,863,957 A | 1/1999 | Li et al. |
| 5,866,099 A | 2/1999 | Owen et al. |

| | | |
|---|---|---|
| 5,866,430 A | 2/1999 | Grow |
| 5,869,241 A | 2/1999 | Edwards et al. |
| 5,872,170 A | 2/1999 | Mine et al. |
| 5,872,623 A * | 2/1999 | Stabile et al. .................. 356/73 |
| 5,876,605 A | 3/1999 | Kitajima et al. |
| 5,891,656 A | 4/1999 | Zarling et al. |
| 5,914,042 A | 6/1999 | Ball et al. |
| 5,922,617 A | 7/1999 | Wang et al. |
| 5,942,443 A | 8/1999 | Parce et al. |
| 5,965,590 A | 10/1999 | Rossignol |
| 5,965,695 A | 10/1999 | Simon et al. |
| 5,980,704 A | 11/1999 | Cherukuri et al. |
| 5,981,297 A | 11/1999 | Baselt |
| 5,985,120 A | 11/1999 | Cholli et al. |
| 5,992,820 A | 11/1999 | Fare et al. |
| 6,008,031 A | 12/1999 | Modrich et al. |
| 6,013,440 A | 1/2000 | Lipshutz et al. |
| 6,023,540 A | 2/2000 | Walt et al. |
| 6,037,137 A | 3/2000 | Komoriya et al. |
| 6,045,579 A | 4/2000 | Hochshuler et al. |
| 6,048,732 A | 4/2000 | Anslyn et al. |
| 6,063,581 A | 5/2000 | Sundrehagen |
| 6,074,616 A | 6/2000 | Buechler et al. |
| 6,083,761 A | 7/2000 | Kedar et al. |
| 6,083,763 A | 7/2000 | Balch |
| 6,103,479 A | 8/2000 | Taylor |
| 6,127,139 A | 10/2000 | Te Koppele et al. |
| 6,133,047 A | 10/2000 | Elaissari et al. |
| 6,140,044 A * | 10/2000 | Besemer et al. ................ 435/6 |
| 6,151,973 A | 11/2000 | Geysen et al. |
| 6,168,948 B1 | 1/2001 | Anderson et al. |
| 6,171,489 B1 | 1/2001 | Ballard et al. |
| 6,171,780 B1 | 1/2001 | Pham et al. |
| 6,197,503 B1 | 3/2001 | Vo-Dinh et al. |
| 6,207,369 B1 * | 3/2001 | Wohlstadter et al. ........... 435/6 |
| 6,219,566 B1 | 4/2001 | Weersink et al. |
| 6,232,066 B1 | 5/2001 | Felder et al. |
| 6,243,486 B1 | 6/2001 | Weiss |
| 6,245,296 B1 | 6/2001 | Ligler et al. |
| 6,254,830 B1 | 7/2001 | Pivarnik et al. |
| 6,258,229 B1 | 7/2001 | Winarta et al. |
| 6,268,222 B1 | 7/2001 | Chandler et al. |
| 6,288,220 B1 | 9/2001 | Kambara et al. |
| 6,309,889 B1 | 10/2001 | Cutler et al. |
| 6,331,441 B1 | 12/2001 | Balch et al. |
| 6,355,431 B1 | 3/2002 | Chee et al. |
| 6,355,491 B1 | 3/2002 | Zhou et al. |
| 6,406,920 B1 | 6/2002 | Davis et al. |
| 6,413,786 B1 | 7/2002 | Hansen et al. |
| 6,482,593 B2 | 11/2002 | Walt et al. |
| 6,485,690 B1 | 11/2002 | Pfost et al. |
| 6,488,872 B1 | 12/2002 | Beebe et al. |
| 6,488,897 B2 | 12/2002 | Dunbrow et al. |
| 6,514,415 B2 | 2/2003 | Hatch |
| 6,529,271 B1 | 3/2003 | Engelhardt |
| 6,577,777 B1 | 6/2003 | Yoshino et al. |
| 6,591,124 B2 | 7/2003 | Sherman |
| 6,601,613 B2 | 8/2003 | McNeely et al. |
| 6,618,140 B2 | 9/2003 | Frost et al. |
| 6,630,307 B2 | 10/2003 | Bruchez et al. |
| 6,632,613 B1 | 10/2003 | Wei et al. |
| 6,638,621 B2 | 10/2003 | Anderson |
| 6,649,403 B1 | 11/2003 | McDevitt et al. |
| 6,654,505 B2 | 11/2003 | Bridgham et al. |
| 6,665,439 B1 | 12/2003 | Takahashi |
| 6,667,177 B1 | 12/2003 | Yabusaki |
| 6,682,649 B1 | 1/2004 | Petersen et al. |
| 6,686,170 B1 | 2/2004 | Flanders et al. |
| 6,692,696 B1 | 2/2004 | Alberte |
| 6,716,629 B2 | 4/2004 | Hess et al. |
| 6,727,058 B2 | 4/2004 | Bushman et al. |
| 6,743,640 B2 | 6/2004 | Whitten et al. |
| 6,770,489 B1 | 8/2004 | Enpuku |
| 6,773,928 B1 | 8/2004 | Yin et al. |
| 6,828,158 B2 | 12/2004 | Eda et al. |
| 6,846,629 B2 | 1/2005 | Sigal et al. |
| 6,855,490 B2 | 2/2005 | Sompuram et al. |
| 6,861,251 B2 | 3/2005 | Green |
| 6,869,570 B2 | 3/2005 | Wardlaw |
| 6,890,742 B2 | 5/2005 | Ammann et al. |
| 6,969,488 B2 * | 11/2005 | Bridgham et al. ............. 422/61 |
| 2001/0002984 A1 | 6/2001 | Vetter |
| 2002/0160363 A1 | 10/2002 | McDevitt et al. |
| 2002/0197622 A1 | 12/2002 | McDevitt et al. |
| 2003/0064422 A1 | 4/2003 | McDevitt et al. |
| 2004/0053322 A1 | 3/2004 | McDevitt et al. |
| 2005/0191620 A1 | 9/2005 | McDevitt et al. |
| 2005/0214863 A1 | 9/2005 | McDevitt et al. |

FOREIGN PATENT DOCUMENTS

| | | |
|---|---|---|
| EP | 0 246 760 | 11/1987 |
| EP | 339 623 | 11/1989 |
| EP | 0 518 557 | 12/1992 |
| GB | 2 300 258 | 10/1996 |
| GB | 2 315 131 | 1/1998 |
| JP | 10-332593 | 12/1998 |
| WO | 90/01069 | 2/1990 |
| WO | 92/00880 | 1/1992 |
| WO | 94/19690 | 9/1994 |
| WO | 97/35189 | 9/1997 |
| WO | 98/17383 | 4/1998 |
| WO | 98/40726 | 9/1998 |
| WO | 98/53300 | 11/1998 |
| WO | 99/17139 | 4/1999 |
| WO | 99/18434 | 4/1999 |
| WO | 99/67024 | 12/1999 |
| WO | 00/04372 | 1/2000 |
| WO | 00/20117 | 4/2000 |

OTHER PUBLICATIONS

International Search Report for International Application No. PCT/US99/16162 mailed Nov. 26, 1999, 12 pages.
Written Opinion for International Application No. PCT/US99/16162 mailed May 2, 2000, 7 pages.
International Preliminary Examination Report for International Application No. PCT/US99/16162 mailed Oct. 12, 2000, 17 pages.
International Search Report for International Application No. PCT/US00/19302 mailed Feb. 22, 2001, 4pages.
International Search Report for International Application No. PCT/US02/03277 mailed Feb. 13, 2002, 5 pages.
International Preliminary Examination Report for International Application No. PCT/US00/19302 mailed Oct. 12, 2001, 5 pages.
International Search Report for International Application No. PCT/US00/19351 mailed Feb. 22, 2001, 5 pages.
International Preliminary Examination Report for International Application No. PCT/US00/19351 mailed Aug. 14, 2001, 17 pages.
International Search Report for International Application No. PCT/US00/19350 mailed Feb. 22, 2001, 5 pages.
International Search Report for International Application No. PCT/US02/03275 mailed May 7, 2003, 6 pages.
International Preliminary Examination Report for International Application No. PCT/US00/19350 mailed Aug. 14, 2001, 14 pages.
Examiner's Report for Australian Application No. 53165/99 mailed May 2, 2002, 3 pages.
Examiner's Report for Australian Application No. 53165/99 mailed May 5, 2003, 2 pages.
International Search Report for International Application No. PCT/US01/03316 mailed May 7, 2001, 8 pages.
International Search Report for International Application No. PCT/US01/03139 mailed May 7, 2001, 8 pages.
International Search Report for International Application No. PCT/US01/03240 mailed May 7, 2001, 9 pages.
Written Opinion for International Application No. PCT/US01/03240 mailed Jan. 22, 2002, 6 pages.

International Preliminary Examination Report for International Application No. PCT/US01/03240 mailed Jun. 6, 2002, 5 pages.
International Search Report for International Application No. PCT/US01/03241 mailed May 7, 2001, 8 pages.
Office Communication for European Application No. 00975164.5 mailed Jun. 4, 2003, 4 pages.
Office Communication for European Application No. 00975164.5 mailed Feb. 11, 2004, 4 pages.
Examiner's Report for Australian Application No. 13255/01 mailed Sep. 3, 2003, 2 pages.
Office Communication for European Application No. 010905306.5 mailed Jan. 23, 2003, 6 pages.
Office Communication for European Application No. 010905306.5 mailed Feb. 16, 2004, 4 pages.
European Search Report for European Application No. 02713535.9 mailed Feb. 18, 2004, 3 pages.
International Search Report for International Application No. PCT/US03/12951 mailed Oct. 14, 2003, 8 pages.
International Search Report for International Application No. PCT/US03/23131 mailed Dec. 12, 2003, 7 pages.
Written Opinion for International Application No. PCT/US03/23131 mailed Feb. 24, 2004, 5 pages.
International Preliminary Examination Report for International Application No. PCT/US03/23131 mailed May 18, 2004, 12 pages.
International Search Report and Written Opinion for International Application No. PCT/US04/03751 mailed Aug. 20, 2004, 9 pages.
International Search Report for International Application No. PCT/US04/03610 mailed Jan. 25, 2005, 3 pages.
Partial Search Report for International Application No. PCT/US2004/041633 mailed Jun. 17, 2005, 6 pages.
International Search Report and Written Opinion for International Application No. PCT/US2004/041633 mailed Nov. 14, 2005.
Co-Pending U.S. Appl. No. 10/470,646, filed Jan. 24, 2005; available in Private PAIR.
Co-Pending U.S. Appl. No. 10/522,499, filed Jan. 24, 2005; available in Private PAIR.
Co-Pending U.S. Appl. No. 10/552,926, filed Jan. 24, 2005;available in Private PAIR.
Co-Pending U.S. Appl. No. 11/022,176, filed Dec. 22, 2004; available in Private PAIR.
Co-Pending U.S. Appl. No. 11/020,442, filed Dec. 22, 2004; available in Private PAIR.
Co-Pending U.S. Appl. No. 11/022,365, filed Dec. 22, 2004; available in Private PAIR.
Co-Pending U.S. Appl. No. 11/021,219, filed Dec. 22, 2004; available in Private PAIR.
Adler, M; Nicholson, J.D.; Hackley, B.E., Jr. "Efficacy of a novel metalloprotease inhibitor on botulinum neurotoxin B activity" FEBS Lett., 1998, 429, 234-238.
Cho et al., "An Unnatural Biopolymer," Science, 1993, 261, p. 1303-1305.
Dickinson et al., "Convergent, Self-Encoded Bead Sensor Arrays in the Design of an Artificial Nose", Anal. Chem., Jun. 1, 1999, vol. 71, No. 11, pp. 2192-2198.
Dickinson et al., "Convergent, Self-Encoded Bead Sensor Arrays in the Design of an Artificial Nose", Anal. Chem., Jun. 1, 1999, vol. 71, No. 11, pp. 2192-2198.
Förster, Th. Transfer Mechanisms of Electronic Excitation;, Discuss. Faraday Soc., 1959, 27, 7.
Goldrick, M.M.; Kimball, G.R.; Liu, Q.: Martin, L.A.; Sommer, S.S.: Tseng, J.Y.H.; "Nirca™-A Rapid Robust Method for Screening for Unknown Point Mutations", Biotechniques, 1996, 21, 106-112.
Grate et al., "Hydrogen Bond Acidic Polymers for Surface Acoustic Wave Vapor Sensors and Arrays," Analytical Chemistry, vol. 71, No. 5, Mar. 1, 1999, pp. 1033-1040.
Hamasaki, K; Ikeda, H.; Nakamura, A.; Ueno, A.; Toda, F.: Suzuki, I.; Osa, T. "Fluorescent Sensors of Molecular Recognition. Modified Cyclodextrins Capable of Exhibiting Guest-Responsive Twisted Intramolecular Charge Transfer Fluorescence", J. Am. Chem. Soc., 1993, 115, 5035.
Han et al, "Deflection behavior of Fabry-Perot pressure sensors having planar and corrugated diaphragms," Microelectronics Research Center and Department of Electrical and Computer Engineering, Feb. 4, 1997.

Han et al., "Fabrication and characterization of a Fabry-Perot based chemical sensor," Microelectronics Research Center and Department of Electrical and Computer Engineering, Feb. 7, 1997.
Healey et al., "Fast Temporal Response Fiber-Optic Chemical Sensors Based on the Photodeposition of Micrometer-Scale Polymer Arrays," Analytical Chemistry, vol. 69, No. 11, Jun. 1, 1997, pp. 2213-2216.
Holtz et al., "Intelligent Polymerized Crystalline Colloidal Arrays: Novel Chemical Sensor Materials," Analytical Chemistry, vol. 70, No. 4, Feb. 15, 1998, pp. 780-791.
Hsu, I.C.; Yang, Q.P.; Kahng, M.W.;Xu, J.F.; "Detection of DNA Point Mutations with DNA Mismatch Repaire Enzymes", Carcinogenesis, 1994, 15, 1657-1662.
Johnson et al., "Identification of Multiple Analytes Using an Optical Sensor Array and Pattern Recognition Neural Networks," Analytical Chemistry, vol. 69, No. 22, Nov. 15, 1997, pp. 4641-4648.
Kaiser, E.; Colescott, R. L.; Bossinger, C. D.; Cook, P.I.; "Color Test for Detection of Free Terminal Amino Groups in the Solid-Phase Synthesis of Peptides", Anal. Biochem., 1970, 34, 595-598.
Khanna, P. L., Ullman, E. F. "4', 5'-Dimethoxyl-6-carboxyfluorescein; A novel dipoledipole coupled fluorescence energy transfer acceptor useful for fluorescence immunoassays", Anal. Bioshem. 1980, 108, 156.
Lauritzen et al., "Peptide Dot Immunoassay and Iimmunoblotting: Electroblotting from Aluminum Thin-layer Chromatography Plates and Isoelectric Focusing Gels to Activated Nitrocellulose," Electrophoresis, 1993, 14, p. 852-859.
Lavigne et al., "Solution-Based Analysis of Multiple Analytes by a Sensor Array: Toward the Development of an Electronic Tongue," J. Am. Chem. Soc., vol. 120, No. 25, Jun. 11, 1998, pp. 6429-6430.
Ludwig, R.; Harada, T.; Ueda, K.; James, T. D.; Shinkai, S. J. Chem. Soc. Perkin Trans 2. 1994, 4, 497.
Michael et al., "Making Sensors out of Disarray: Optical Sensor Microarray" SPIE, 1998, vol. 3270, pp. 34-41.
Morrison, L. E. "Time resolved Detection of Energy Transfer: Theory and Application to Immunoassays", Anal. Biochem. 1998, 174, 101.
Niikura, K;Metzger, A.; Anslyn, E.V., "A Sensing Ensemble with Selectivity for Iositol Triphosphate", J. Am. Chem. Soc., 1998, 120, 0000.
Potyrailo et al., "Optical Time-of-Flight Chemical Detection: Absorption-Modulated Fluorescence for Spatially Resolved Analyte Mapping in a Bidirectional Distributed Fiber-Optic Sensor," Analytical Chemistry, vol. 70, No. 16, Aug. 15, 1998, pp. 3407-3412.
Ricco et al., "Surface Acoustic Wave Chemical Sensor Arrays; New Chemically Sensitive Interfaces Combined with Novel Cluster Analysis to Detect Volatile Organic Compounds and Mixtures," Accounts of Chemical Research, vol. 31, No. 5, 1998, pp. 289-296.
Schmidt, J.J.; Stafford, R.G.; Bostian, K.A.; "Type A botulinum neurotoxin proteolytic activity: development of competitve inhibitors and implicatins for substrate specificity at the $S_1'$ binding subsite", FEBS Lett., 1998, 435, 61-64.
Schutz, et al., "Direct Observation of Ligand Colocalization on Indivdual Receptor Molecules," Biophysical Journal, 1998, 74, 2223-2226.
Shinkai, S.; Tsukagoshi, K.; Ishikawa, Y.; Kunitake, T.J. Chem. Soc. Chem. Commun. 1991, 1039.
Shiomi, Y.; Saisho, M.; Tsukagoshi, k.; Shinkai, S.J. Chem. Soc. Perkin Trans I 1993, 2111.
Shone, C.C.; Roberts, A.K., "Peptide substrate specificity and properties of the zincendopetidase activity of botulinum type B neurotoxin", Eur. J. Biochem., 1994, 225, 263-270.
Soleihac, J.-M.; Cornille, F.; Martin, L.; Lenoir, C.; Fournie-Zaluski, M.-C.; Roques, B.P. A senstive and rapid fluorescence-based assay for determination of tetanus toxin peptidase activity: Anal. Biochem., 1996, 241, 120-127.
White et al., "Rapid Analyte Recognition in a Device Based on Optical Sensors and Olfactory System," Analytical Chemistry, vol. 68, No. 13, Jul. 1, 1996, pp. 2191-2202.
Youil R; Kemper, B; Cotton, RGH, "Detection of 81 of 81 Known Mouse Beta-Goblin Promoter Mutations with T4 Endonuclease-VII-The EMC Method", Genomics, 1996, 32, 431-500.

* cited by examiner

Peptides

Nucleotides

Polythioureas

Polyguanidiniums

US 7,491,552 B2

FLUID BASED ANALYSIS OF MULTIPLE ANALYTES BY A SENSOR ARRAY

PRIORITY CLAIM

This application is a divisional of U.S. patent application Ser. No. 09/287,248, filed Apr. 7, 1999, now U.S. Pat. No. 6,908,770 to McDevitt et al. issued on Jun. 21, 2005 which claims priority to U.S. Provisional Application No. 60/093,111 entitled "FLUID BASED ANALYSIS OF MULTIPLE ANALYTES BY A SENSOR ARRAY" filed on Jul. 16, 1998.

STATEMENT REGARDING FEDERALLY SPONSORED RESEARCH OR DEVELOPMENT

Research leading to this invention was federally supported, in part, by grant No. 1R01GM57306-01 entitled "The Development of an Electronic Tongue" from the National Institute of Health and the U.S. Government has certain rights to this invention.

BACKGROUND OF THE INVENTION

1. Field of the Invention

The present invention relates to a method and device for the detection of analytes in a fluid. More particularly, the invention relates to the development of a sensor array system capable of discriminating mixtures of analytes, toxins, and/or bacteria in medical, food/beverage, and environmental solutions.

2. Brief Description of the Related Art

The development of smart sensors capable of discriminating different analytes, toxins, and bacteria has become increasingly important for clinical, environmental, health and safety, remote sensing, military, food/beverage and chemical processing applications. Although many sensors capable of high sensitivity and high selectivity detection have been fashioned for single analyte detection, only in a few selected cases have array sensors been prepared which display solution phase multi-analyte detection capabilities. The advantages of such array systems are their utility for the analysis of multiple analytes and their ability to be "trained" to respond to new stimuli. Such on site adaptive analysis capabilities afforded by the array structures make their utilization promising for a variety of future applications. Array based sensors displaying the capacity to sense and identify complex vapors have been demonstrated recently using a number of distinct transduction schemes. For example, functional sensors based on Surface Acoustic Wave (SAW), tin oxide ($SnO_2$) sensors, conductive organic polymers, and carbon black/polymer composites have been fashioned. The use of tin oxide sensors, for example, is described in U.S. Pat. No. 5,654,497 to Hoffheins et al. These sensors display the capacity to identify and discriminate between a variety of organic vapors by virtue of small site-to-site differences in response characteristics. Pattern recognition of the overall fingerprint response for the array serves as the basis for an olfaction-like detection of the vapor phase analyte species. Indeed, several commercial "electronic noses" have been developed recently. Most of the well established sensing elements are based on $SnO_2$ arrays which have been derivatized so as to yield chemically distinct response properties. Arrays based on SAW crystals yield extremely sensitive responses to vapor, however, engineering challenges have prevented the creation of large SAW arrays having multiple sensor sites. To our knowledge, the largest SAW device reported to date possesses only 12 sensor elements. Additionally, limited chemical diversity and the lack of understanding of the molecular features of such systems makes their expansion into more complex analysis difficult.

Other structures have been developed that are capable of identifying and discriminating volatile organic molecules. One structure involves a series of conductive polymer layers deposited onto metal contacting layers. When these sensors are exposed to volatile reagents, some of the volatile reagents adsorb into the polymer layers, leading to small changes in the electrical resistance of these layers. It is the small differences in the behavior of the various sites that allows for a discrimination, identification, and quantification of the vapors. The detection process takes only a few seconds, and sensitivities of part-per-billion can be achieved with this relatively simple approach. This "electronic nose" system is described in U.S. Pat. No. 5,698,089 to Lewis et al. which is incorporated by reference as if set forth herein.

Although the above described electronic nose provides an impressive capability for monitoring volatile reagents, the system possesses a number of undesirable characteristics that warrant the development of alternative sensor array systems. For example, the electronic nose can be used only for the identification of volatile reagents. For many environmental, military, medical, and commercial applications, the identification and quantification of analytes present in liquid or solid-phase samples is necessary. Moreover, the electronic nose systems are expensive (e.g., the Aromascan system costs about $50,000/unit) and bulky ($\geq 1$ ft$^3$). Furthermore, the functional elements for the currently available electronic nose are composed of conductive polymer systems which possess little chemical selectivity for many of the analytes which are of interest to the military and civilian communities.

One of the most commonly employed sensing techniques has exploited colloidal polymer microspheres for latex agglutination tests (LATs) in clinical analysis. Commercially available LATs for more than 60 analytes are used routinely for the detection of infectious diseases, illegal drugs, and early pregnancy tests. The vast majority of these types of sensors operate on the principle of agglutination of latex particles (polymer microspheres) which occurs when the antibody-derivatized microspheres become effectively "cross-linked" by a foreign antigen resulting in the attachment to, or the inability to pass through a filter. The dye-doped microspheres are then detected calorimetrically upon removal of the antigen carrying solution. However, the LATs lack the ability to be utilized for multiple, real time analyte detection schemes as the nature of the response intrinsically depends on a cooperative effect of the entire collection of microspheres.

Similar to the electronic nose, array sensors that have shown great analytical promise are those based on the "DNA on a chip" technology. These devices possess a high density of DNA hybridization sites that are affixed in a two-dimensional pattern on a planar substrate. To generate nucleotide sequence information, a pattern is created from unknown DNA fragments binding to various hybridization sites. Both radiochemical and optical methods have provided excellent detection limits for analysis of limited quantities of DNA. (Stimpson, D. I.; Hoijer, J. V.; Hsieh, W.; Jou, C.; Gardon, J.; Theriault, T.; Gamble, R.; Baldeschwieler, J. D. Proc. Natl. Acad. Sci. USA 1995, 92, 6379). Although quite promising for the detection of DNA fragments, these arrays are generally not designed for non-DNA molecules, and accordingly show very little sensitivity to smaller organic molecules. Many of the target molecules of interest to civilian and military communities, however, do not possess DNA components. Thus, the need for a flexible, non-DNA based sensor is still desired. Moreover, while a number of prototype DNA chips containing up to a few thousand different nucleic acid probes have been described, the existing technologies tend to be difficult to expand to a practical size. As a result, DNA chips may be prohibitively expensive for practical uses.

A system of analyzing fluid samples using an array formed of heterogeneous, semi-selective thin films which function as sensing receptor units is described in U.S. Pat. No. 5,512,490 to Walt et al., which is incorporated by reference as if set forth herein. Walt appears to describe the use of covalently attached polymeric "cones" which are grown via photopolymerization onto the distal face of fiber optic bundles. These sensor probes appear to be designed with the goal of obtaining unique, continuous, and reproducible responses from small localized regions of dye-doped polymer. The polymer appears to serve as a solid support for indicator molecules that provide information about test solutions through changes in optical properties. These polymer supported sensors have been used for the detection of analytes such as pH, metals, and specific biological entities. Methods for manufacturing large numbers of reproducible sensors, however, has yet to be developed. Moreover, no methods for acquisitions of data streams in a simultaneous manner are commercially available with this system. Optical alignment issues may also be problematic for these systems.

A method of rapid sample analysis for use in the diagnostic microbiology field is also desirable. The techniques now used for rapid microbiology diagnostics detect either antigens or nucleic acids. Rapid antigen testing is based on the use of antibodies to recognize either the single cell organism or the presence of infected cell material. Inherent to this approach is the need to obtain and characterize the binding of the antibody to unique structures on the organism being tested. Since the identification and isolation of the appropriate antibodies is time consuming, these techniques are limited to a single agent per testing module and there is no opportunity to evaluate the amount of agent present.

Most antibody methods are relatively insensitive and require the presence of $10^5$ to $10^7$ organisms. The response time of antibody-antigen reactions in diagnostic tests of this type ranges from 10 to 120 minutes, depending on the method of detection. The fastest methods are generally agglutination reactions, but these methods are less sensitive due to difficulties in visual interpretation of the reactions. Approaches with slower reaction times include antigen recognition by antibody conjugated to either an enzyme or chromophore. These test types tend to be more sensitive, especially when spectrophotometric methods are used to determine if an antigen-antibody reaction has occurred. These detection schemes do not, however, appear to allow the simultaneous detection of multiple analytes on a single detector platform.

The alternative to antigen detection is the detection of nucleic acids. An approach for diagnostic testing with nucleic acids uses hybridization to target unique regions of the target organism. These techniques require fewer organisms ($10^3$ to $10^5$), but require about five hours to complete. As with antibody-antigen reactions this approach has not been developed for the simultaneous detection of multiple analytes.

The most recent improvement in the detection of microorganisms has been the use of nucleic acid amplification. Nucleic acid amplification tests have been developed that generate both qualitative and quantitative data. However, the current limitations of these testing methods are related to delays caused by specimen preparation, amplification, and detection. Currently, the standard assays require about five hours to complete. The ability to complete much faster detection for a variety of microorganisms would be of tremendous importance to military intelligence, national safety, medical, environmental, and food areas.

It is therefore desirable that new sensors capable of discriminating different analytes, toxins, and bacteria be developed for medical/clinical diagnostic, environmental, health and safety, remote sensing, military, food/beverage, and chemical processing applications. It is further desired that the sensing system be adaptable to the simultaneous detection of a variety of analytes to improve throughput during various chemical and biological analytical procedures.

SUMMARY OF THE INVENTION

Herein we describe a system and method for the analysis of a fluid containing one or more analytes. The system may be used for either liquid or gaseous fluids. The system, in some embodiments, may generate patterns that are diagnostic for both the individual analytes and mixtures of the analytes. The system in some embodiments, is made of a plurality of chemically sensitive particles, formed in an ordered array, capable of simultaneously detecting many different kinds of analytes rapidly. An aspect of the system is that the array may be formed using a microfabrication process, thus allowing the system to be manufactured in an inexpensive manner.

In an embodiment of a system for detecting analytes, the system, in some embodiments, includes a light source, a sensor array, and a detector. The sensor array, in some embodiments, is formed of a supporting member which is configured to hold a variety of chemically sensitive particles (herein referred to as "particles") in an ordered array. The particles are, in some embodiments, elements which will create a detectable signal in the presence of an analyte. The particles may produce optical (e.g., absorbance or reflectance) or fluorescence/phosphorescent signals upon exposure to an analyte. Examples of particles include, but are not limited to functionalized polymeric beads, agarous beads, dextrose beads, polyacrylamide beads, control pore glass beads, metal oxides particles (e.g., silicon dioxide ($SiO_2$) or aluminum oxides ($Al_2O_3$)), polymer thin films, metal quantum particles (e.g., silver, gold, platinum, etc.), and semiconductor quantum particles (e.g., Si, Ge, GaAs, etc.). A detector (e.g., a charge-coupled device "CCD") in one embodiment is positioned below the sensor array to allow for the data acquisition. In another embodiment, the detector may be positioned above the sensor array to allow for data acquisition from reflectance of the light off of the particles.

Light originating from the light source may pass through the sensor array and out through the bottom side of the sensor array. Light modulated by the particles may pass through the sensor array and onto the proximally spaced detector. Evaluation of the optical changes may be completed by visual inspection or by use of a CCD detector by itself or in combination with an optical microscope. A microprocessor may be coupled to the CCD detector or the microscope. A fluid delivery system may be coupled to the supporting member of the sensor array. The fluid delivery system, in some embodiments, is configured to introduce samples into and out of the sensor array.

In an embodiment, the sensor array system includes an array of particles. The particles may include a receptor molecule coupled to a polymeric bead. The receptors, in some embodiments, are chosen for interacting with analytes. This interaction may take the form of a binding/association of the receptors with the analytes. The supporting member may be made of any material capable of supporting the particles, while allowing the passage of the appropriate wavelengths of light. The supporting member may include a plurality of cavities. The cavities may be formed such that at least one particle is substantially contained within the cavity.

In an embodiment, the optical detector may be integrated within the bottom of the supporting member, rather than using a separate detecting device. The optical detectors may be coupled to a microprocessor to allow evaluation of fluids without the use of separate detecting components. Additionally, a fluid delivery system may also be incorporated into the supporting member. Integration of detectors and a fluid delivery system into the supporting member may allow the formation of a compact and portable analyte sensing system.

A high sensitivity CCD array may be used to measure changes in optical characteristics which occur upon binding of the biological/chemical agents. The CCD arrays may be interfaced with filters, light sources, fluid delivery and micromachined particle receptacles, so as to create a functional sensor array. Data acquisition and handling may be performed with existing CCD technology. CCD detectors may be configured to measure white light, ultraviolet light or fluorescence. Other detectors such as photomultiplier tubes, charge induction devices, photo diodes, photodiode arrays, and microchannel plates may also be used.

A particle, in some embodiments, possess both the ability to bind the analyte of interest and to create a modulated signal. The particle may include receptor molecules which posses the ability to bind the analyte of interest and to create a modulated signal. Alternatively, the particle may include receptor molecules and indicators. The receptor molecule may posses the ability to bind to an analyte of interest. Upon binding the analyte of interest, the receptor molecule may cause the indicator molecule to produce the modulated signal. The receptor molecules may be naturally occurring or synthetic receptors formed by rational design or combinatorial methods. Some examples of natural receptors include, but are not limited to, DNA, RNA, proteins, enzymes, oligopeptides, antigens, and antibodies. Either natural or synthetic receptors may be chosen for their ability to bind to the analyte molecules in a specific manner.

In one embodiment, a naturally occurring or synthetic receptor is bound to a polymeric bead in order to create the particle. The particle, in some embodiments, is capable of both binding the analyte(s) of interest and creating a detectable signal. In some embodiments, the particle will create an optical signal when bound to an analyte of interest.

A variety of natural and synthetic receptors may be used. The synthetic receptors may come from a variety of classes including, but not limited to, polynucleotides (e.g., aptamers), peptides (e.g., enzymes and antibodies), synthetic receptors, polymeric unnatural biopolymers (e.g., polythioureas, polyguanidiniums), and imprinted polymers. Polynucleotides are relatively small fragments of DNA which may be derived by sequentially building the DNA sequence. Peptides include natural peptides such as antibodies or enzymes or may be synthesized from amino acids. Unnatural biopolymers are chemical structure which are based on natural biopolymers, but which are built from unnatural linking units. For example, polythioureas and polyguanidiniums have a structure similar to peptides, but may be synthesized from diamines (i.e., compounds which include at least two amine functional groups) rather than amino acids. Synthetic receptors are designed organic or inorganic structures capable of binding various analytes.

In an embodiment, a large number of chemical/biological agents of interest to the military and civilian communities may be sensed readily by the described array sensors. Bacteria may also be detected using a similar system. To detect, sense, and identify intact bacteria, the cell surface of one bacteria may be differentiated from other bacteria, or genomic material may be detected using oligonucleic receptors. One method of accomplishing this differentiation is to target cell surface oligosaccharides (i.e., sugar residues). The use of synthetic receptors which are specific for oligosaccharides may be used to determine the presence of specific bacteria by analyzing for cell surface oligosaccharides.

BRIEF DESCRIPTION OF THE DRAWINGS

The above brief description as well as further objects, features and advantages of the methods and apparatus of the present invention will be more fully appreciated by reference to the following detailed description of presently preferred but nonetheless illustrative embodiments in accordance with the present invention when taken in conjunction with the accompanying drawings in which.

DETAILED DESCRIPTION OF PREFERRED EMBODIMENTS

Herein we describe a system and method for the simultaneous analysis of a fluid containing multiple analytes. The system may be used for either liquid or gaseous fluids. The system may generate patterns that are diagnostic for both individual analytes and mixtures of the analytes. The system, in some embodiments, is made of a combination of chemically sensitive particles, formed in an ordered array, capable of simultaneously detecting many different kinds of analytes rapidly. An aspect of the system is that the array may be formed using a microfabrication process, thus allowing the system to be manufactured in an inexpensive manner.

System For Analysis of Analytes

Figure 1:
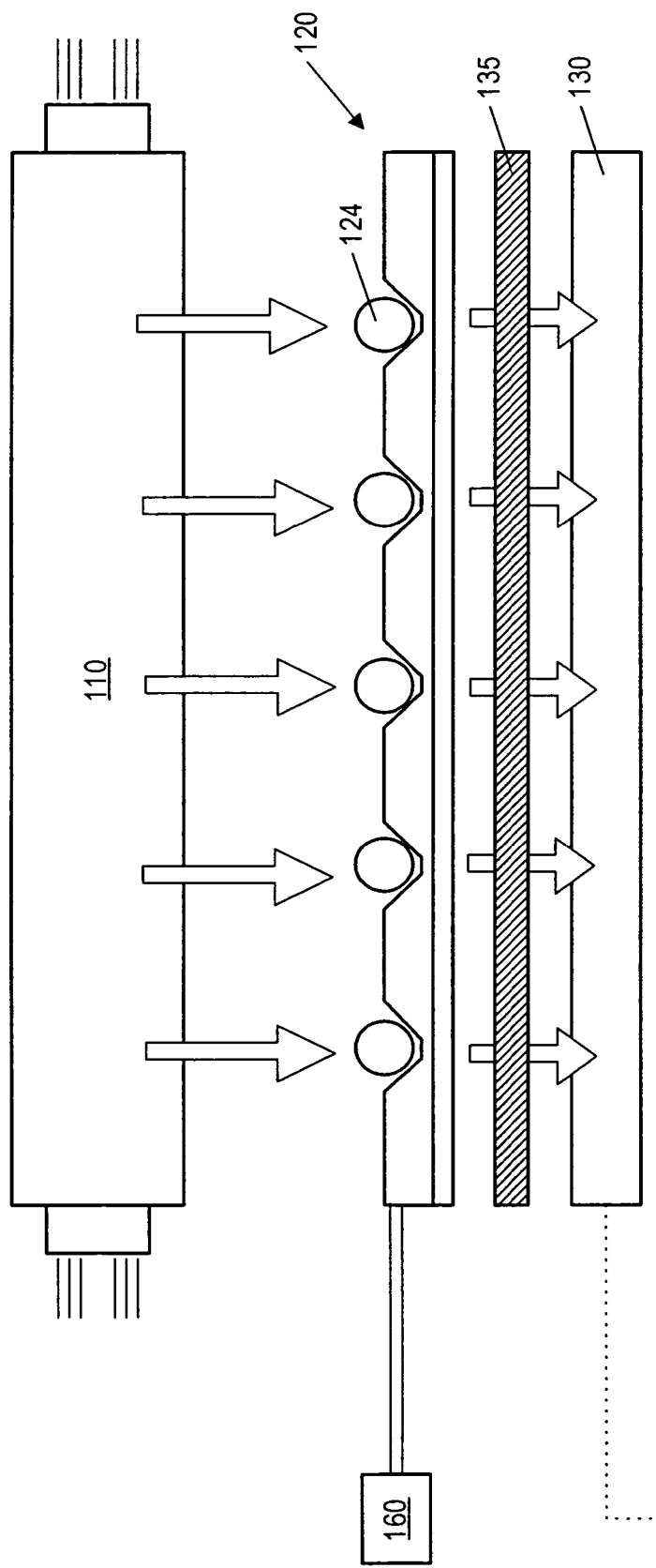
FIG. 1 depicts a schematic of an analyte detection system.

Shown in FIG. 1 is an embodiment of a system for detecting analytes in a fluid. The system, in some embodiments, includes a light source 110, a sensor array 120 and a detector 130. The light source 110 may be a white light source or light emitting diodes (LED). In one embodiment, light source 110 may be a blue light emitting diode (LED) for use in systems relying on changes in fluorescence signals. For colorimetric (e.g., absorbance) based systems, a white light source may be used. The sensor array 120, in some embodiments, is formed of a supporting member which is configured to hold a variety of particles 124. A detecting device 130 (e.g., a charge-coupled device "CCD") may be positioned below the sensor array to allow for data acquisition. In another embodiment, the detecting device 130 may be positioned above the sensor array.

Light originating from the light source 110, in some embodiments, passes through the sensor array 120 and out through the bottom side of the sensor array. The supporting member and the particles together, in some embodiments, provide an assembly whose optical properties are well matched for spectral analyses. Thus, light modulated by the particles may pass through the sensor array and onto the proximally spaced detector 130. Evaluation of the optical changes may be completed by visual inspection (e.g., with a microscope) or by use of a microprocessor 140 coupled to the detector. For fluorescence measurements, a filter 135 may be placed between supporting member 120 and detector 130 to remove the excitation wavelength. A fluid delivery system 160 may be coupled to the supporting member. The fluid delivery system 160 may be configured to introduce samples into and out of the sensor array.

In an embodiment, the sensor array system includes an array of particles. Upon the surface and within the interior region of the particles are, in some embodiments, located a variety of receptors for interacting with analytes. The supporting member, in some embodiments, is used to localize these particles as well as to serve as a microenvironment in which the chemical assays can be performed. For the chemical/biological agent sensor arrays, the particles used for analysis are about 0.05-500 microns in diameter, and may actually change size (e.g., swell or shrink) when the chemical environment changes. Typically, these changes occur when the array system is exposed to the fluid stream which includes the analytes. For example, a fluid stream which comprises a non-polar solvent, may cause non-polar particles to change in volume when the particles are exposed to the solvent. To accommodate these changes, it is preferred that the supporting member consist of an array of cavities which serve as micro test-tubes.

The supporting member may be made of any material capable of supporting the particles, while allowing the passage of the appropriate wavelength of light. The supporting member is also made of a material substantially impervious to the fluid in which the analyte is present. A variety of materials may be used including plastics, glass, silicon based materials (e.g., silicon, silicon dioxide, silicon nitride, etc.) and metals. In one embodiment, the supporting member includes a plurality of cavities. The cavities may be formed such that at least one particle is substantially contained within the cavity. Alternatively, a plurality of particles may be contained within a single cavity.

In an embodiment, the supporting member may consist of a strip of plastic which is substantially transparent to the wavelength of light necessary for detection. A series of cavities may be formed within the strip. The cavities may be configured to hold at least one particle. The particles may be contained within the strip by a transparent cover which is configured to allow passage of the analyte containing fluid into the cavities.

Figure 2:
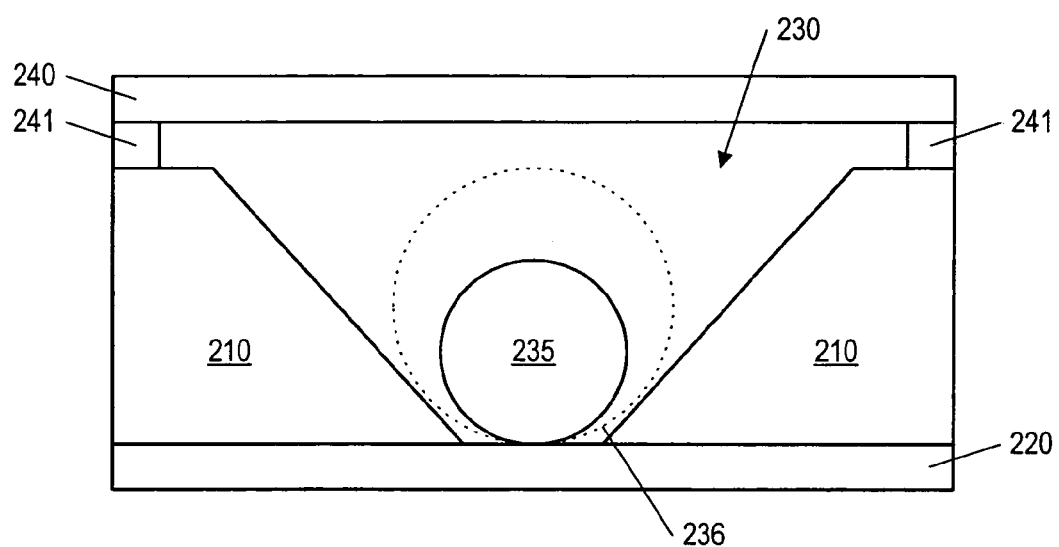
FIG. 2 depicts a particle disposed in a cavity.

In another embodiment, the supporting member may be formed using a silicon wafer as depicted in FIG. 2. The silicon wafer 210 may include a substantially transparent layer 220 formed on the bottom surface of the wafer. The cavities 230, in one embodiment, are formed by an anisotropic etch process of the silicon wafer. In one embodiment, anisotropic etching of the silicon wafer is accomplished using a wet hydroxide etch. Photolithographic techniques may be used to define the locations of the cavities. The cavities may be formed such that the sidewalls of the cavities are substantially tapered at an angle of between about 50 to 60 degrees. Formation of such angled cavities may be accomplished by wet anisotropic etching of <100> silicon. The term "<100> silicon" refers to the crystal orientation of the silicon wafer. Other types of silicon, (e.g., <110> and <111> silicon) may lead to steeper angled sidewalls. For example, <111> silicon may lead to sidewalls formed at about 90 degrees. The angled sides of the cavities in some embodiments, serve as "mirror layers" which may improve the light collection efficiency of the cavities. The etch process may be controlled so that the formed cavities extend through the silicon wafer to the upper surface of transparent layer 220. While depicted as pyramidal, the cavities may be formed in a number of shapes including but not limited to, spherical, oval, cubic, or rectangular. An advantage to using a silicon wafer for the support member, is that the silicon material is substantially opaque to the light produced from the light source. Thus, the light may be inhibited from passing from one cavity to adjacent cavities. In this manner, light from one cavity may be inhibited from influencing the spectroscopic changes produced in an adjacent cavity.

The silicon wafer, in some embodiments, has an area of approximately 1 cm$^2$ to about 100 cm$^2$ and includes about $10^1$ to about $10^6$ cavities. In an embodiment, about 100 cavities are formed in a ten by ten matrix. The center to center distance between the cavities, in some embodiments, is about 500 microns. Each of the cavities may include at least one particle.

The transparent layer 220 may serve as a window, allowing light of a variety of wavelengths to pass through the cavities 230 and to the detector. Additionally, the transparent layer may serve as a platform onto which the individual particles 235 may be positioned. The transparent layer may be formed of silicon dioxide ($SiO_2$), silicon nitride ($Si_3N_4$) or silicon dioxide/silicon nitride multi-layer stacks. The transparent layer, in some embodiments, is deposited onto the silicon wafer prior to the formation of the cavities.

The cavities 230 may be sized to substantially contain a particle 235. The cavities are, in some embodiments, larger than a particle. The cavities are, in some embodiments, sized to allow facile placement and removal of the particle within the cavities. The cavity may be substantially larger than the particle, thus allowing the particle to swell during use. For example, a particle may have a size as depicted in FIG. 2 by particle 235. During use, contact with a fluid (e.g., a solvent) may cause the particle to swell, for example, to a size depicted as circle 236. In some embodiments, the cavity is sized to allow such swelling of the particle during use. A particle may be positioned at the bottom of a cavity using, e.g., a micromanipulator. After a particle has been placed within the cavity, a transparent cover plate 240 may be placed on top of the supporting member to keep the particle in place.

When forming an array which includes a plurality of particles, the particles may be placed in the array in an ordered fashion using the micromanipulator. In this manner, a ordered array having a predefined configuration of particles may be formed. Alternatively, the particles may be randomly placed within the cavities. The array may subsequently undergo a calibration test to determine the identity of the particle at any specified location in the supporting member.

The transparent cover plate 240, in some embodiments, is coupled to the upper surface of the silicon wafer 220 such that the particles are inhibited from becoming dislodged from the cavity. The transparent cover plate, in some embodiments, is positioned a fixed distance above the silicon wafer, as depicted in FIG. 2, to keep the particle in place, while allowing the entrance of fluids into the cavities. The transparent cover plate, in some embodiments, is positioned at a distance above the substrate which is substantially less than a width of the particle. The transparent cover plate may be made of any material which is substantially transparent to the wavelength of light being utilized by the detector. The transparent cover plate may be made of plastic, glass, quartz, or silicon dioxide/silicon nitride.

In one embodiment, the transparent cover plate 240, is a thin sheet of glass (e.g., a microscope slide cover slip). The slide may be positioned a fixed distance above the silicon wafer. Support structures 241 (See FIG. 2) may be placed upon the silicon wafer 210 to position the transparent cover plate 240. The support structures 20 may be formed from a polymer or a silicon based material. In another embodiment, a polymeric substrate is coupled to the silicon wafer to form the support structures 241 for the transparent cover plate 240. In an embodiment, a plastic material with an adhesive backing (e.g., cellophane tape) is positioned on the silicon wafer 210. After the support structures 241 are placed on the wafer the transparent cover plate 240 is placed upon the support structures. The support structures inhibit the transparent cover sheet from contacting the silicon wafer 200. In this manner, a channel is formed between the silicon wafer and the transparent cover plate which allow the fluid to pass into the cavity, while inhibiting displacement of the particle by the fluid.

Figure 3:
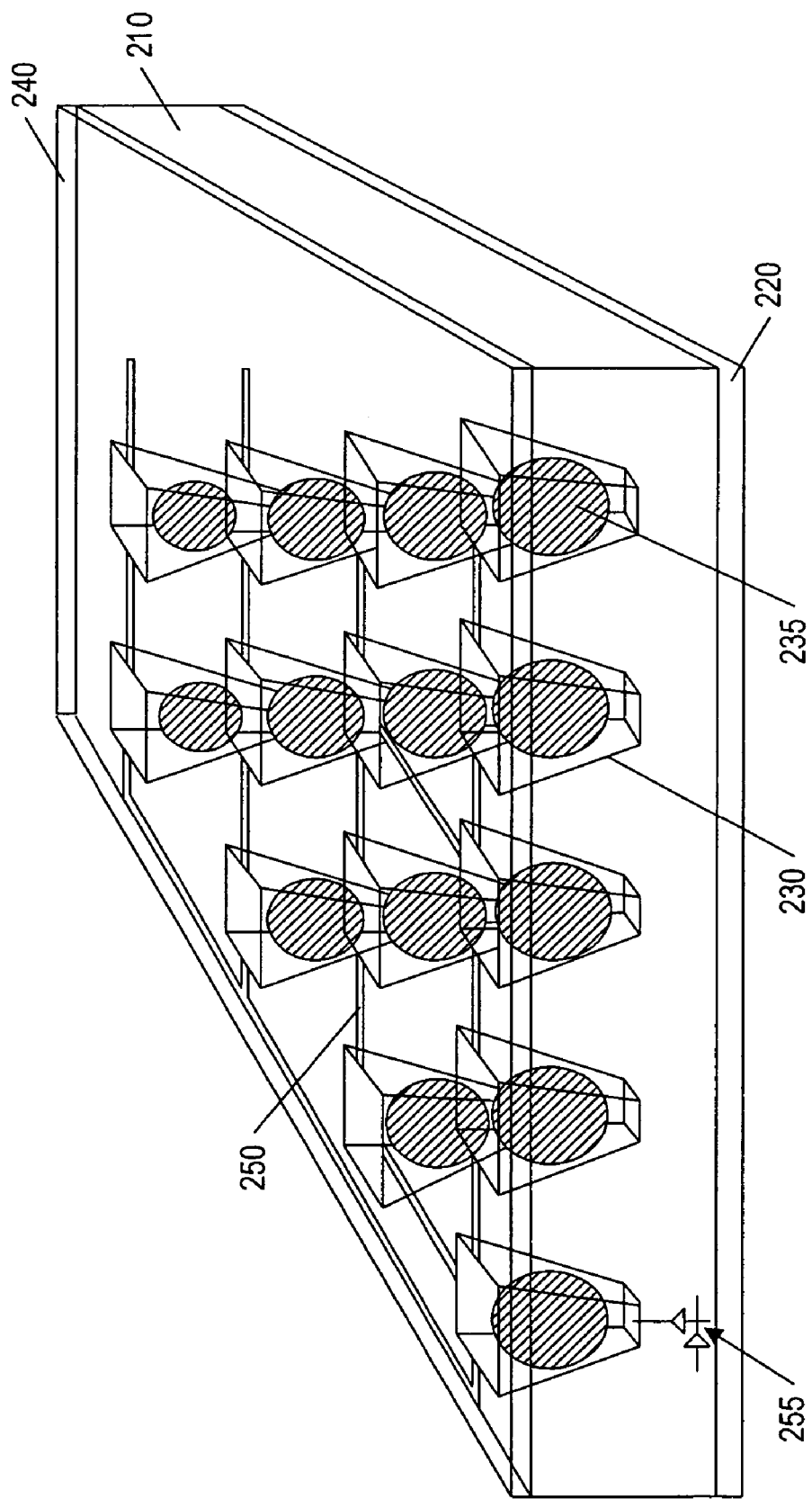
FIG. 3 depicts a sensor array.

In another embodiment, the transparent cover plate 240 may be fastened to the upper surface of the silicon wafer, as depicted in FIG. 3. In this embodiment, the fluid may be inhibited from entering the cavities 230 by the transparent cover plate 240. To allow passage of the fluid into the cavities, a number of channels 250 may be formed in the silicon wafer. The channels, in one embodiment, are oriented to allow passage of the fluid into substantially all of the cavities. When contacted with the fluid, the particles may swell to a size which may plug the channels. To prevent this plugging, the channels may be formed near the upper portion of the cavities, as depicted in FIG. 3. The channels, in one embodiment, are formed using standard photolithographic masking to define the regions where the trenches are to be formed, followed by the use of standard etching techniques. A depth of the cavity may be such that the particle resides substantially below the position of the channel. In this way, the plugging of the channels due to swelling of the particle may be prevented.

The inner surfaces of the cavities may be coated with a material to aid the positioning of the particles within the cavities. In one embodiment, a thin layer of gold or silver may be used to line the inner surface of the cavities. The gold or silver layer may act as an anchoring surface to anchor particles (e.g., via alkylthiol bonding). In addition, the gold or silver layer may also increase the reflectivity of the inner surface of the cavities. The increased reflectance of the surface may enhance the analyte detection sensitivity of the system. Alternatively, polymer layers and self-assembled monolayers formed upon the inner surface of the cavities may be used to control the particle adhesion interactions. Additional chemical anchoring methods may be used for silicon surfaces such as those based on siloxane type reagents, which may be attached to Si—OH functionalities. Similarly, monomeric and polymeric reagents attached to an interior region of the cavities can be used to alter the local wetting characteristics of the cavities. This type of methodology can be used to anchor the particles as well as to alter the fluid delivery characteristics of the cavity. Furthermore, amplification of the signals for the analytes may be accomplished with this type of strategy by causing preconcentration of appropriate analytes in the appropriate type of chemical environment.

In another embodiment, the optical detector may be integrated within the bottom transparent layer 220 of the supporting member, rather than using a separate detecting device. The optical detectors may be formed using a semiconductor-based photodetector 255. The optical detectors may be coupled to a microprocessor to allow evaluation of fluids without the use of separate detecting components. Additionally, the fluid delivery system may also be incorporated into the supporting member. Micro-pumps and micro-valves may also be incorporated into the silicon wafer to aid passage of the fluid through the cavities. Integration of detectors and a fluid delivery system into the supporting member may allow the formation of a compact and portable analyte sensing system. Optical filters may also be integrated into the bottom membrane of the cavities. These filters may prevent short wavelength excitation from producing "false" signals in the optical detection system (e.g., a CCD detector array) during fluorescence measurements.

A sensing cavity may be formed on the bottom surface of the support substrate. An example of a sensing cavity that may be used is a Fabry-Perot type cavity. Fabry-Perot cavity-based sensors may be used to detect changes in optical path length induced by either a change in the refractive index or a change in physical length of the cavity. Using micromachining techniques, Fabry-Perot sensors may be formed on the bottom surface of the cavity.

Figure 4A:
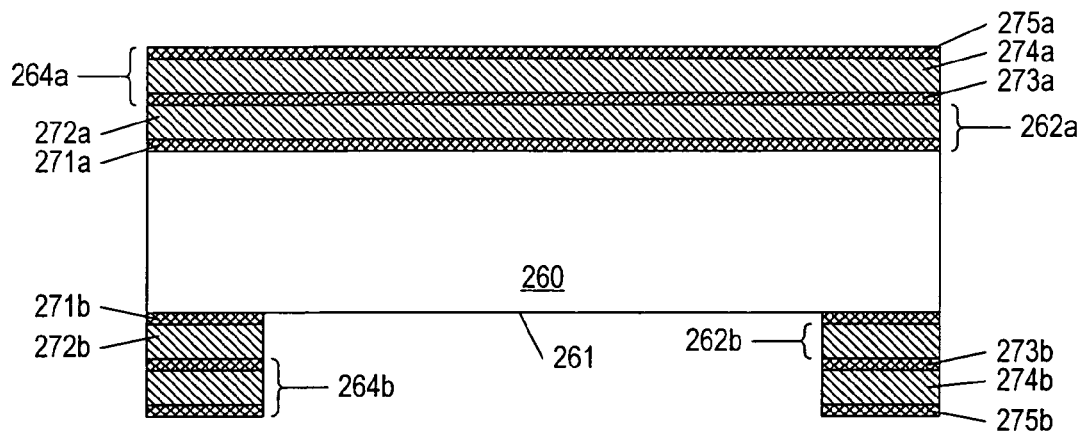
FIG. 4A-F depicts the formation of a Fabry-Perot cavity on the back of a sensor array.

FIGS. 4A-F depict a sequence of processing steps for the formation of a cavity and a planar top diaphragm Fabry-Perot sensor on the bottom surface of a silicon based supporting member. A sacrificial barrier layer 262a/b is deposited upon both sides of a silicon supporting member 260. The silicon supporting member 260 may be a double-side polished silicon wafer having a thickness ranging from about 100 µm to about 500 µm, preferably from about 200 µm to about 400 µm, and more preferably of about 300 µm. The barrier layer 262a/b may be composed of silicon dioxide, silicon nitride, or silicon oxynitride. In one embodiment, the barrier layer 262a/b is composed of a stack of dielectric materials. As depicted in FIG. 4A, the barrier layer 262a/b is composed of a stack of dielectric materials which includes a silicon nitride layer 271a/b and a silicon dioxide layer 272a/b. Both layers may be deposited using a low pressure chemical vapor deposition ("LPCVD") process. Silicon nitride may be deposited using an LPCVD reactor by reaction of ammonia ($NH_3$) and dichlorosilane ($SiCl_2H_2$) at a gas flow rate of about 3.5:1, a temperature of about 800° C., and a pressure of about 220 mTorr. The silicon nitride layer 271a/b is deposited to a thickness in the range from about 100 Å to about 500 Å, preferably from 200 Å to about 400 Å, and more preferably of about 300 Å. Silicon dioxide is may be deposited using an LPCVD reactor by reaction of silane ($SiH_4$) and oxygen ($O_2$) at a gas flow rate of about 3:4, a temperature of about 450° C., and a pressure of about 110 mTorr. The silicon dioxide layer 272a/b is deposited to a thickness in the range from about 3000 Å to about 7000 Å, preferably from 4000 Å to about 6000 Å, and more preferably of about 5000 Å. The front face silicon dioxide layer 272a, in one embodiment, acts as the main barrier layer. The underlying silicon nitride layer 271a acts as an intermediate barrier layer to inhibit overetching of the main barrier layer during subsequent KOH wet anisotropic etching steps.

A bottom diaphragm layer 264a/b is deposited upon the barrier layer 262a/b on both sides of the supporting member 260. The bottom diaphragm layer 264a/b may be composed of silicon nitride, silicon dioxide, or silicon oxynitride. In one embodiment, the bottom diaphragm layer 264a/b is composed of a stack of dielectric materials. As depicted in FIG. 4A, the bottom diaphragm layer 264a/b is composed of a stack of dielectric materials which includes a pair of silicon nitride layers 273a/b and 275a/b surrounding a silicon dioxide layer 274a/b. All of the layers may be deposited using an LPCVD process. The silicon nitride layers 273a/b and 275a/b have a thickness in the range from about 500 Å to about 1000 Å, preferably from 700 Å to about 800 Å, and more preferably of about 750 Å. The silicon dioxide layer 274a/b has a thickness in the range from about 3000 Å to about 7000 Å, preferably from 4000 Å to about 6000 Å, and more preferably of about 4500 Å.

Figure 4B:
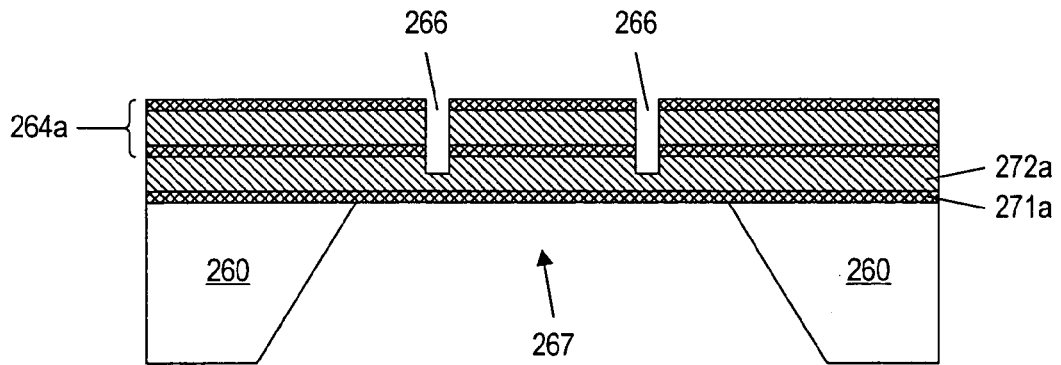

A cavity which will hold the particle may now be formed in the supporting member 260. The bottom diaphragm layer 264b and the barrier layer 262b formed on the back side 261 of the silicon supporting member 260 are patterned and etched using standard photolithographic techniques. In one embodiment, the layers are subjected to a plasma etch process. The plasma etching of silicon dioxide and silicon nitride may be performed using a mixture of carbontetrafluoride ($CF_4$) and oxygen ($O_2$). The patterned back side layers 262b and 264b may be used as a mask for anisotropic etching of the silicon supporting member 260. The silicon supporting member 260, in one embodiment, is anisotropically etched with a 40% potassium hydroxide ("KOH") solution at 80° C. to form the cavity. The etch is stopped when the front side silicon nitride layer 271a is reached, as depicted in FIG. 4B. The silicon nitride layer 271a inhibits etching of the main barrier layer 272a during this etch process. The cavity 267 may be formed extending through the supporting member 260. After formation of the cavity, the remaining portions of the back side barrier layer 262b and the diaphragm layer 264b may be removed.

Etch windows 266 are formed through the bottom diaphragm layer 264a on the front side of the wafer. A masking layer (not shown) is formed over the bottom diaphragm layer 264a and patterned using standard photolithographic techniques. Using the masking layer, etch windows 266 may be formed using a plasma etch. The plasma etching of silicon dioxide and silicon nitride may be performed using a mixture of carbontetrafluoride ($CF_4$) and oxygen ($O_2$). The etching is continued through the bottom diaphragm layer 264a and partially into the barrier layer 262a. In one embodiment, the etching is stopped at approximately half the thickness of the barrier layer 262a. Thus, when the barrier layer 262a is subsequently removed the etch windows 266 will extend through the bottom diaphragm layer 264a, communicating with the cavity 267. By stopping the etching at a midpoint of the barrier layer, voids or discontinuities may be reduced since the bottom diaphragm is still continuous due to the remaining barrier layer.

Figure 4C:
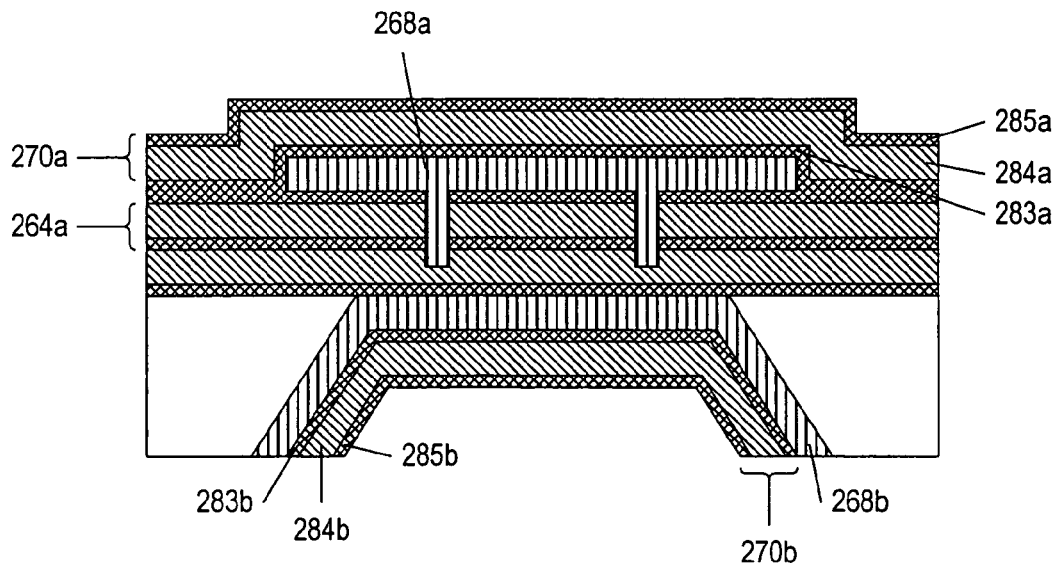

After the etch windows 266 are formed, a sacrificial spacer layer 268a/b is deposited upon the bottom diaphragm layer 264a and within cavity 267, as depicted in FIG. 4C. The spacer layer may be formed from LPCVD polysilicon. In one embodiment, the front side deposited spacer layer 268a will also at least partially fill the etch windows 266. Polysilicon may be deposited using an LPCVD reactor using silane ($SiH_4$) at a temperature of about 650° C. The spacer layer 268a/b is deposited to a thickness in the range from about 4000 Å to about 10,000 Å, preferably from 6000 Å to about 8000 Å, and more preferably of about 7000 Å. The preferred thickness of the spacer layer 268a is dependent on the desired thickness of the internal air cavity of the Fabry-Perot detector. For example, if a Fabry-Perot detector which is to include a 7000 Å air cavity between the top and bottom diaphragm layer is desired, a spacer layer having a thickness of about 7000 Å would be formed. After the spacer layer has been deposited, a masking layer for etching the spacer layer 268a (not shown) is used to define the etch regions of the spacer layer 268a. The etching may be performed using a composition of nitric acid ($HNO_3$), water, and hydrogen fluoride (HF) in a ratio of 25:13:1, respectively, by volume. The lateral size of the subsequently formed cavity is determined by the masking pattern used to define the etch regions of the spacer layer 268a.

After the spacer layer 268a has been etched, the top diaphragm layer 270a/b is formed. The top diaphragm 270a/b, in one embodiment, is deposited upon the spacer layer 268a/b on both sides of the supporting member. The top diaphragm 270a/b may be composed of silicon nitride, silicon dioxide, or silicon oxynitride. In one embodiment, the top diaphragm 270a/b is composed of a stack of dielectric materials. As depicted in FIG. 4C, the top diaphragm 270a/b is composed of a stack of dielectric materials which includes a pair of silicon nitride layers 283a/b and 285a/b surrounding a silicon dioxide layer 284a/b. All of the layers may be deposited using an LPCVD process. The silicon nitride layers 283a/b and 285a/b have a thickness in the range from about 1000 Å to about 2000 Å, preferably from 1200 Å to about 1700 Å, and more preferably of about 1500 Å. The silicon dioxide layer 284a/b has a thickness in the range from about 5000 Å to about 15,500 Å, preferably from 7500 Å to about 12,000 Å, and more preferably of about 10,500 Å.

Figure 4D:
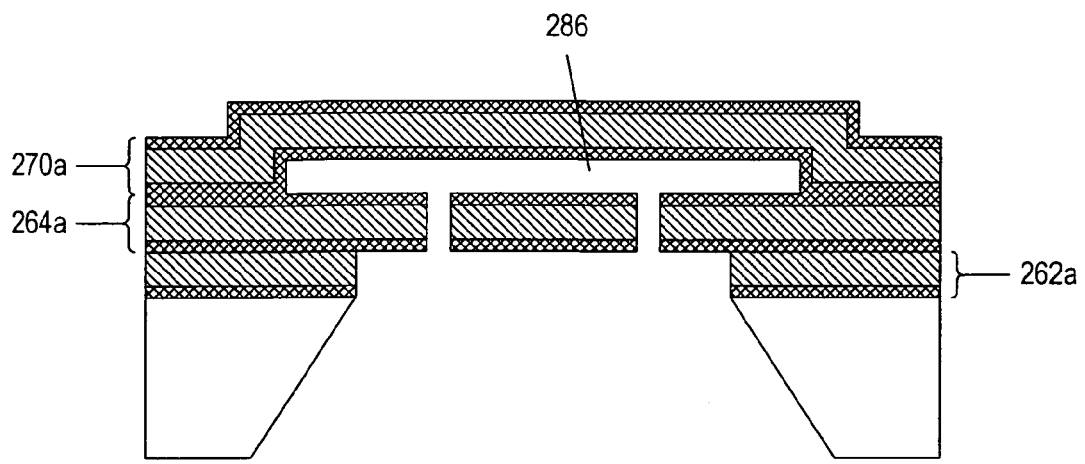

After depositing the top diaphragm 270a/b, all of the layers stacked on the bottom face of the supporting member (e.g., layers 268b, 283b, 284b, and 285b) are removed by multiple wet and plasma etching steps, as depicted in FIG. 4D. After these layers are removed, the now exposed portions of the barrier layer 262a are also removed. This exposes the spacer layer 268a which is present in the etch windows 266. The spacer layer 268 may be removed from between the top diaphragm 270a and the bottom diaphragm 264a by a wet etch using a KOH solution, as depicted in FIG. 4D. Removal of the spacer material 268a, forms a cavity 286 between the top diaphragm layer 270a and the bottom diaphragm layer 264a. After removal of the spacer material, the cavity 286 may be washed using deionized water, followed by isopropyl alcohol to clean out any remaining etching solution.

Figure 4E:
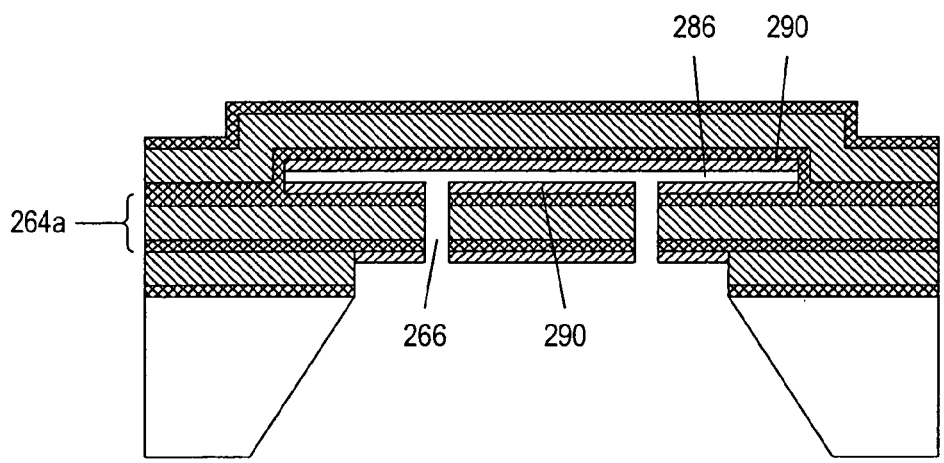

The cavity 286 of the Fabry-Perot sensor may be filled with a sensing substrate 290, as depicted in FIG. 4E. To coat the cavity 286 with a sensing substrate 290, the sensing substrate may be dissolved in a solvent. A solution of the sensing substrate is applied to the supporting member 260. The solution is believed to rapidly enter the cavity 286 through the etched windows 266 in the bottom diaphragm 264a, aided in part by capillary action. As the solvent evaporates, a thin film of the sensing substrate 290 coats the inner walls of the cavity 286, as well as the outer surface of the bottom diaphragm 264a. By repeated treatment of the supporting member with the solution of the sensing substrate, the thickness of the sensing substrate may be varied.

In one embodiment, the sensing substrate 290 is poly(3-dodecylthiophene) whose optical properties change in response to changes in oxidation states. The sensing substrate poly(3-dodecylthiophene) may be dissolved in a solvent such as chloroform or xylene. In one embodiment, a concentration of about 0.1 g of poly(3-dodecylthiophene)/mL is used. Application of the solution of poly(3-dodecylthiophene) to the supporting member causes a thin film of poly(3-dodecylthiophene) to be formed on the inner surface of the cavity.

Figure 4F:
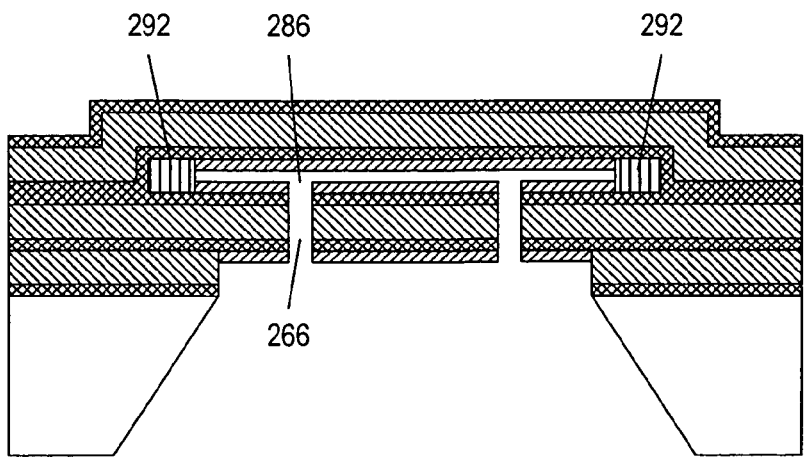

In some instances, the sensing substrate, when deposited within a cavity of a Fabry-Perot type detector, may cause stress in the top diaphragm of the detector. It is believed that when a sensing polymer coats a planar top diaphragm, extra residual stress on the top diaphragm causes the diaphragm to become deflected toward the bottom diaphragm. If the deflection becomes to severe, sticking between the top and bottom diaphragms may occur. In one embodiment, this stress may be relieved by the use of supporting members 292 formed within the cavity 286, as depicted in FIG. 4F. The supporting members 292 may be formed without any extra processing steps to the above described process flow. The formation of supporting members may be accomplished by deliberately leaving a portion of the spacer layer within the cavity. This may be accomplished by underetching the spacer layer (e.g., terminating the etch process before the entire etch process is finished). The remaining spacer will behave as a support member to reduce the deflection of the top diaphragm member. The size and shape of the support members may be adjusted by altering the etch time of the spacer layer, or adjusting the shape of the etch windows 266.

In another embodiment, a high sensitivity CCD array may be used to measure changes in optical characteristics which occur upon binding of the biological/chemical agents. The CCD arrays may be interfaced with filters, light sources, fluid delivery and micromachined particle receptacles, so as to create a functional sensor array. Data acquisition and handling may be performed with existing CCD technology. Data streams (e.g., red, green, blue for colorimetric assays; gray intensity for fluorescence assays) may be transferred from the CCD to a computer via a data acquisition board. Current CCDs may allow for read-out rates of $10^5$ pixels per second. Thus, the entire array of particles may be evaluated hundreds of times per second allowing for studies of the dynamics of the various host-guest interaction rates as well as the analyte/polymer diffusional characteristics. Evaluation of this data may offer a method of identifying and quantifying the chemical/biological composition of the test samples. CCD detectors may be configured to measure white light, ultraviolet light or fluorescence. Other detectors such as photomultiplier tubes, charge induction devices, photodiode, photodiode arrays, and microchannel plates may also be used. It should be understood that while the detector is depicted as being positioned under the supporting member, the detector may also be positioned above the supporting member. It should also be understood that the detector typically includes a sensing element for detecting the spectroscopic events and a component for displaying the detected events. The display component may be physically separated from the sensing element. The sensing element may be positioned above or below the sensor array while the display component is positioned close to a user.

In one embodiment, a CCD detector may be used to record color changes of the chemical sensitive particles during analysis. As depicted in FIG. 1, a CCD detector 130 may be placed beneath the supporting member 120. The light transmitted through the cavities is captured and analyzed by the CCD detector. In one embodiment, the light is broken down into three color components, red, green and blue. To simplify the data, each color is recorded using 8 bits of data. Thus, the data for each of the colors will appear as a value between 0 and 255. The color of each chemical sensitive element may be represented as a red, blue and green value. For example, a blank particle (i.e., a particle which does not include a receptor) will typically appear white. For example, when broken down into the red, green and blue components, it is found that a typical blank particle exhibits a red value of about 253, a green value of about 250, and a blue value of about 222. This signifies that a blank particle does not significantly absorb red, green or blue light. When a particle with a receptor is scanned, the particle may exhibit a color change, due to absorbance by the receptor. For example, it was found that when a particle which includes a 5-carboxyfluorescein receptor is subjected to white light, the particle shows a strong absorbance of blue light. The CCD detector values for the 5-carboxyfluorescein particle exhibits a red value of about 254, a green value of about 218, and a blue value of about 57. The decrease in transmittance of blue light is believed to be due to the absorbance of blue light by the 5-carboxyfluorescein. In this manner, the color changes of a particle may be quantitatively characterized. An advantage of using a CCD detector to monitor the color changes is that color changes which may not be noticeable to the human eye may now be detected.

The support array may be configured to allow a variety of detection modes to be practiced. In one embodiment, a light source is used to generate light which is directed toward the particles. The particles may absorb a portion of the light as the light illuminates the particles. The light then reaches the detector, reduced in intensity by the absorbance of the particles. The detector may be configure to measure the reduction in light intensity (i.e., the absorbance) due to the particles. In another embodiment, the detector may be placed above the supporting member. The detector may be configured to measure the amount of light reflected off of the particles. The absorbance of light by the particles is manifested by a reduction in the amount of light being reflected from the cavity. The light source in either embodiment may be a white light source or a fluorescent light source.

Chemically Sensitive Particles

A particle, in some embodiments, possess both the ability to bind the analyte of interest and to create a modulated signal. The particle may include receptor molecules which posses the ability to bind the analyte of interest and to create a modulated signal. Alternatively, the particle may include receptor molecules and indicators. The receptor molecule may posses the ability to bind to an analyte of interest. Upon binding the analyte of interest, the receptor molecule may cause the indicator molecule to produce the modulated signal. The receptor molecules may be naturally occurring or synthetic receptors formed by rational design or combinatorial methods. Some examples of natural receptors include, but are not limited to, DNA, RNA, proteins, enzymes, oligopeptides, antigens, and antibodies. Either natural or synthetic receptors may be chosen for their ability to bind to the analyte molecules in a specific manner. The forces which drive association/recognition between molecules include the hydrophobic effect, anion-cation attraction, and hydrogen bonding. The relative strengths of these forces depend upon factors such as the solvent dielectric properties, the shape of the host molecule, and how it complements the guest. Upon host-guest association, attractive interactions occur and the molecules stick together. The most widely used analogy for this chemical interaction is that of a "lock and key". The fit of the key molecule (the guest) into the lock (the host) is a molecular recognition event.

A naturally occurring or synthetic receptor may be bound to a polymeric resin in order to create the particle. The polymeric resin may be made from a variety of polymers including, but not limited to, agarous, dextrose, acrylamide, control pore glass beads, polystyrene-polyethylene glycol resin, polystyrene-divinyl benzene resin, formylpolystyrene resin, trityl-polystyrene resin, acetyl polystyrene resin, chloroacetyl polystyrene resin, arninomethyl polystyrene-divinylbenzene resin, carboxypolystyrene resin, chloromethylated polystyrene-divinylbenzene resin, hydroxymethyl polystyrene-divinylbenzene resin, 2-chlorotrityl chloride polystyrene resin, 4-benzyloxy-2'4'-dimethoxybenzhydrol resin (Rink Acid resin), triphenyl methanol polystyrene resin, diphenylmethanol resin, benzhydrol resin, succinimidyl carbonate resin, p-nitrophenyl carbonate resin, imidazole carbonate resin, polyacrylamide resin, 4-sulfamylbenzoyl-4'-methylbenzhydrylamine-resin (Safety-catch resin), 2-amino-2-(2'-nitrophenyl)propionic acid-aminomethyl resin (ANP Resin), p-benzyloxybenzyl alcohol-divinylbenzene resin (Wang resin), p-methylbenzhydrylamine-divinylbenzene resin (MBHA resin), Fmoc-2,4-dimethoxy-4'-(carboxymethyloxy)-benzhydrylamine linked to resin (Knorr resin), 4-(2',4'-Dimethoxyphenyl-Fmoc-aminomethyl)-phenoxy resin (Rink resin), 4-hydroxymethyl-benzoyl-4'-methylbenzhydrylamine resin (HMBA-MBHA Resin), p-nitrobenzophenone oxime resin (Kaiser oxime resin), and amino-2,4-dimethoxy-4'-(carboxymethyloxy)-benzhydrylamine handle linked to 2-chlorotrityl resin (Knorr-2-chlorotrityl resin). In one embodiment, the material used to form the polymeric resin is compatible with the solvent in which the analyte is dissolved. For example, polystyrene-divinyl benzene resin will swell within non-polar solvents, but does not significantly swell within polar solvents. Thus, polystyrene-divinyl benzene resin may be used for the analysis of analytes within non-polar solvents. Alternatively, polystyrene-polyethylene glycol resin will swell with polar solvents such as water. Polystyrene-polyethylene glycol resin may be useful for the analysis of aqueous fluids.

Figure 5:
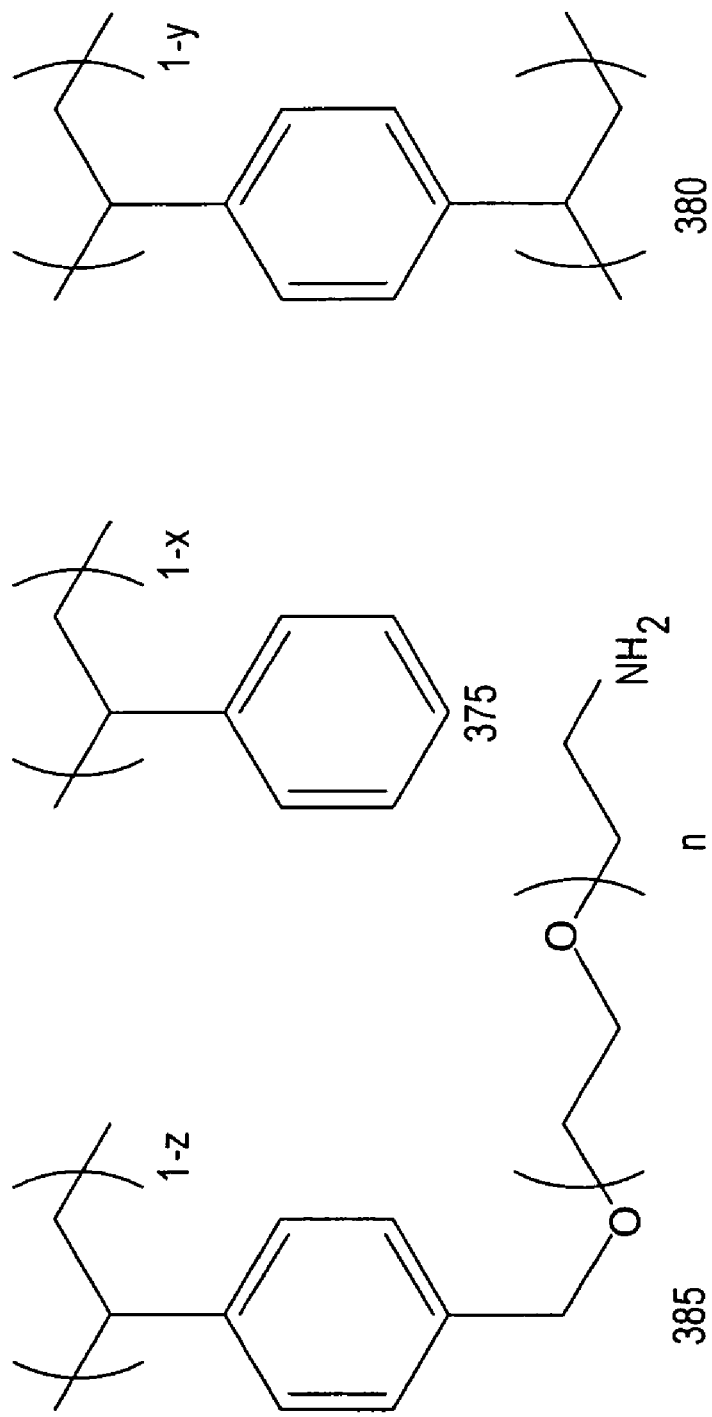
FIG. 5 depicts the chemical constituents of a particle.

In one embodiment, a polystyrene-polyethylene glycol-divinyl benzene material is used to form the polymeric resin. The polystyrene-polyethylene glycol-divinyl benzene resin is formed from a mixture of polystyrene 375, divinyl benzene 380 and polystyrene-polyethylene glycol 385, see FIG. 5. The polyethylene glycol portion of the polystyrene-polyethylene glycol 385, in one embodiment, may be terminated with an amine. The amine serves as a chemical handle to anchor both receptors and indicator dyes. Other chemical functional groups may be positioned at the terminal end of the polyethylene glycol to allow appropriate coupling of the polymeric resin to the receptor molecules or indicators.

The chemically sensitive particle, in one embodiment, is capable of both binding the analyte(s) of interest and creating a detectable signal. In one embodiment, the particle will create an optical signal when bound to an analyte of interest. The use of such a polymeric bound receptors offers advantages both in terms of cost and configurability. Instead of having to synthesize or attach a receptor directly to a supporting member, the polymeric bound receptors may be synthesized en masse and distributed to multiple different supporting members. This allows the cost of the sensor array, a major hurdle to the development of mass-produced environmental probes and medical diagnostics, to be reduced. Additionally, sensor arrays which incorporate polymeric bound receptors may be reconfigured much more quickly than array systems in which the receptor is attached directly tot he supporting member. For example, if a new variant of a pathogen or a pathogen that contains a genetically engineered protein is a threat, then a new sensor array system may be readily created to detect these modified analytes by simply adding new sensor elements (e.g., polymeric bound receptors) to a previously formed supporting member.

Figure 6:
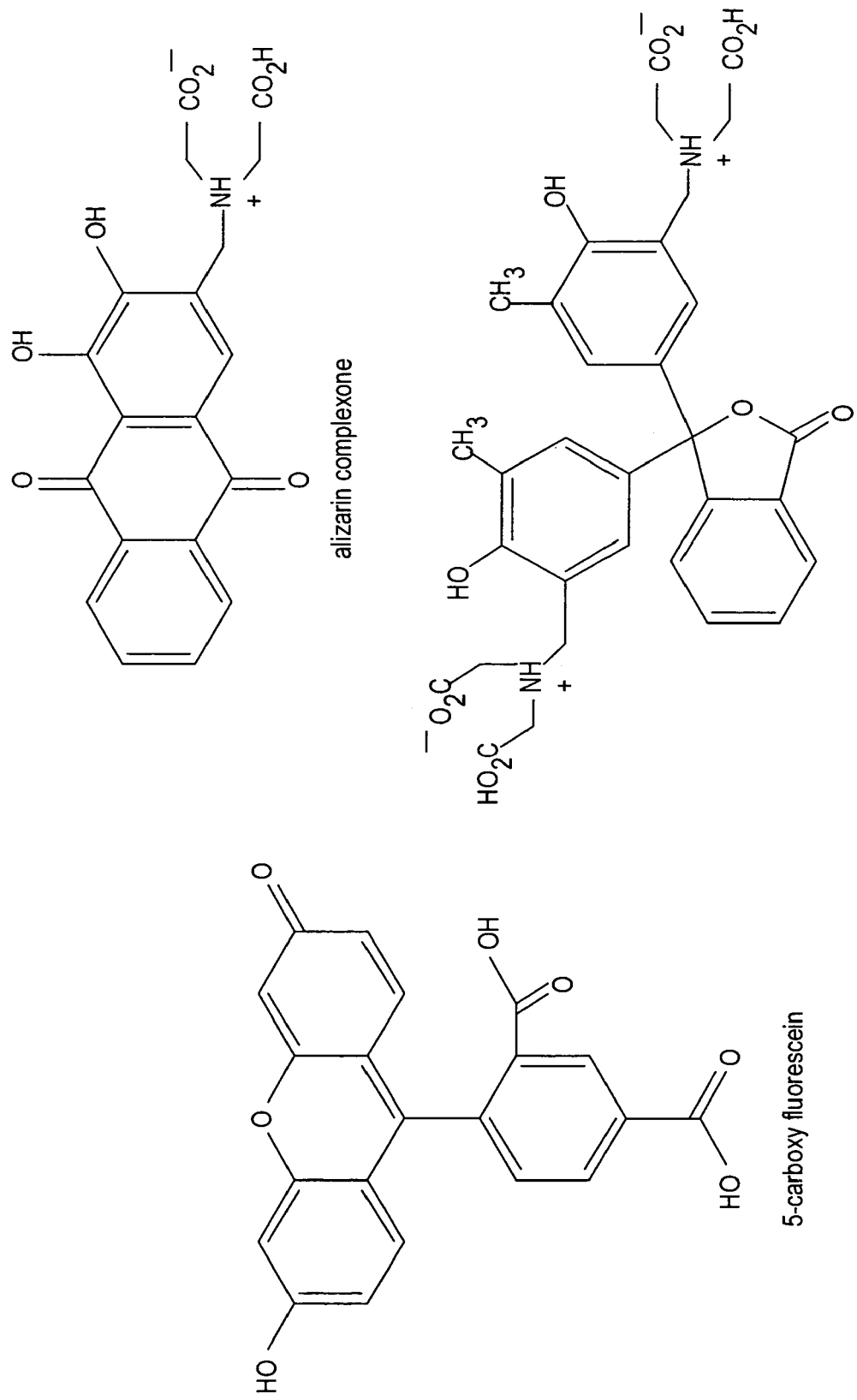
FIG. 6 depicts the chemical formulas of some receptor compounds.

In one embodiment, a receptor, which is sensitive to changes in the pH of a fluid sample is bound to a polymeric resin to create a particle. That is, the receptor is sensitive to the concentration of hydrogen cations ($H^+$). The receptor in this case is typically sensitive to the concentration of $H^+$ in a fluid solution. The analyte of interest may therefore be $H^+$. There are many types of molecules which undergo a color change when the pH of the fluid is changed. For example, many types of dyes undergo significant color changes as the pH of the fluid medium is altered. Examples of receptors which may be used to monitor the pH of a fluid sample include 5-carboxyfluorescein and alizarin complexone, depicted in FIG. 6. Each of these receptors undergoes significant color changes as the pH of the fluid is altered. 5-carboxyfluorescein undergoes a change from yellow to orange as the pH of the fluid is increased. Alizarin complexone undergoes two color changes, first from yellow to red, then from red to blue as the pH of the fluid increases. By monitoring the change in color caused by dyes attached to a polymeric particle, the pH of a solution may be qualitatively and, with the use of a detector (e.g., a CCD detector), quantitatively monitored.

In another embodiment, a receptor which is sensitive to presence of metal cations is bound to a polymeric particle to create a particle. The receptor in this case is typically sensitive to the concentration of one or more metal cations present in a fluid solution. In general, colored molecules which will bind cations may be used to determine the presence of a metal cation in a fluid solution. Examples of receptors which may be used to monitor the presence of cations in a fluid sample include alizarin complexone and o-cresolphthalein complexone, see FIG. 6. Each of these receptors undergoes significant color changes as the concentration of a specific metal ion in the fluid is altered. Alizarin complexone is particularly sensitive to lanthanum ions. In the absence of lanthanum, alizarin complexone will exhibit a yellow color. As the concentration of lanthanum is increased, alizarin complexone will change to a red color. o-Cresolphthalein complexone is particularly sensitive to calcium ions. In the absence of calcium, o-cresolphthalein complexone is colorless. As the concentration of calcium is increased, o-cresolphthalein complexone will change to a blue color. By monitoring the change in color of metal cation sensitive receptors attached to a polymeric particle, the presence of a specific metal ion may be qualitatively and, with the use of a detector (e.g., a CCD detector), quantitatively monitored.

Figure 7:
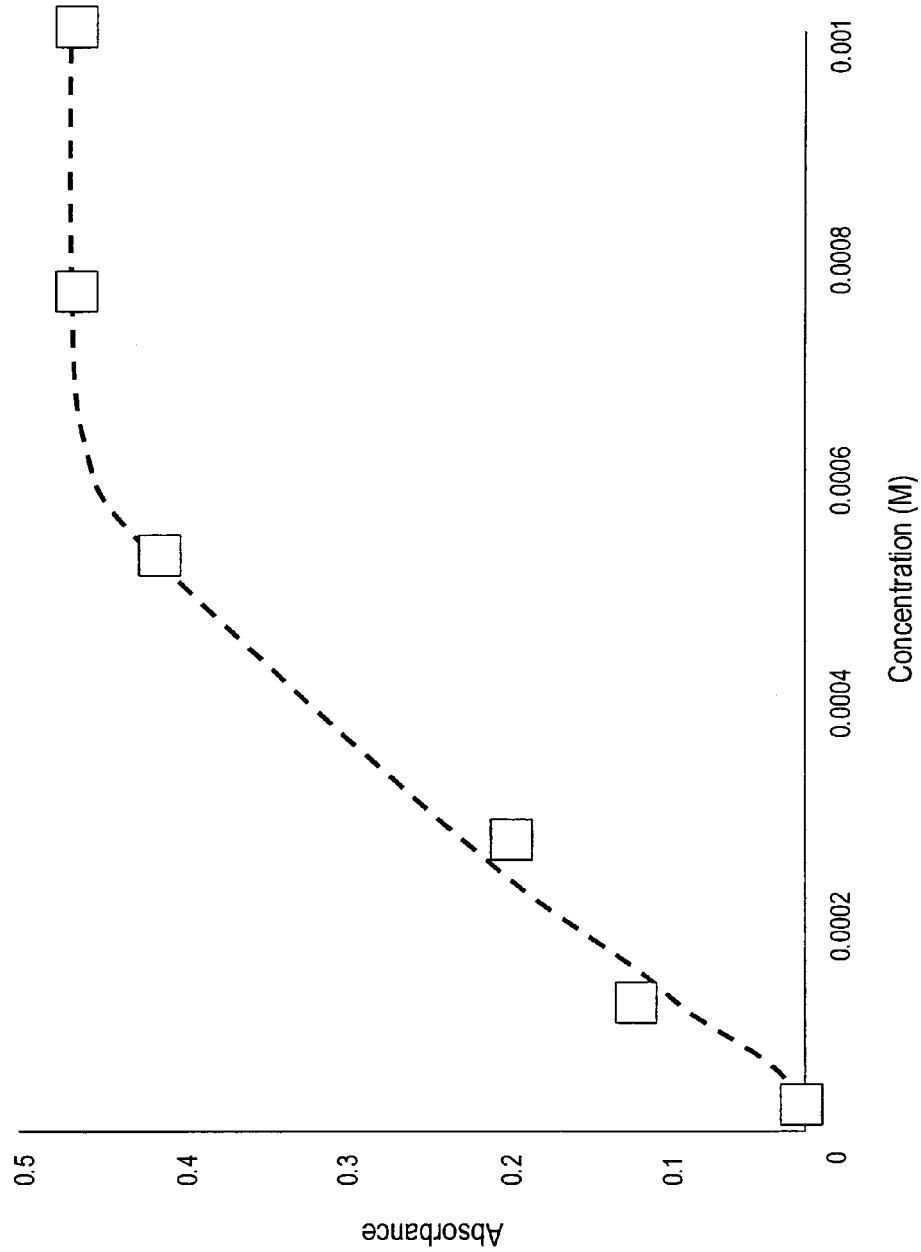
FIG. 7 depicts a plot of the absorbance of green light vs. concentration of calcium ($Ca^{+2}$) for a particle which includes an o-cresolphthalein complexone receptor.

Referring to FIG. 7, a graph of the absorbance of green light vs. concentration of calcium ($Ca^{+2}$) is depicted for a particle which includes an o-cresolphthalein complexone receptor. As the concentration of calcium is increased, the absorbance of green light increases in a linear manner up to a concentration of about 0.0006 M. A concentration of 0.0006 M is the solubility limit of calcium in the fluid, thus no significant change in absorbance is noted after this point. The linear relationship between concentration and absorbance allows the concentration of calcium to be determined by measuring the absorbance of the fluid sample.

In one embodiment, a detectable signal may be caused by the altering of the physical properties of an indicator ligand bound to the receptor or the polymeric resin. In one embodiment, two different indicators are attached to a receptor or the polymeric resin. When an analyte is captured by the receptor, the physical distance between the two indicators may be altered such that a change in the spectroscopic properties of the indicators is produced. A variety of fluorescent and phosphorescent indicators may be used for this sensing scheme.

This process, known as Forster energy transfer, is extremely sensitive to small changes in the distance between the indicator molecules.

Figure 8:
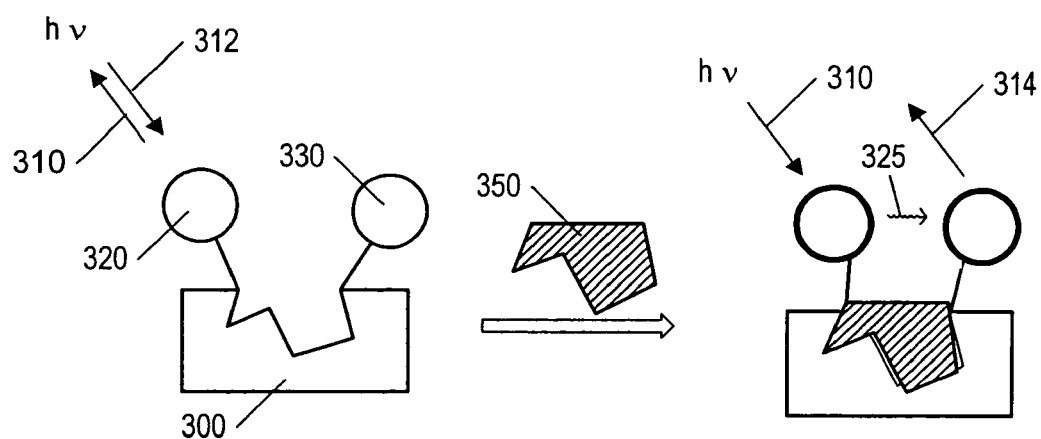
FIG. 8 depicts a schematic view of the transfer of energy from a first indicator to a second indicator in the presence of an analyte.

For example, a first fluorescent indicator 320 (e.g., a fluorescein derivative) and a second fluorescent indictor 330 (e.g., a rhodamine derivative) may be attached to a receptor 300, as depicted in FIG. 8. When no analyte is present short wavelength excitation 310 may excite the first fluorescent indicator 320, which fluoresces as indicated by 312. The short wavelength excitation, however, may cause little or no fluorescence of the second fluorescent indicator 330. After binding of analyte 350 to the receptor, a structural change in the receptor molecule may bring the first and second fluorescent indicators closer to each other. This change in intermolecular distance may allow the excited first indicator 320 to transfer a portion of its fluorescent energy 325 to the second fluorescent indicator 330. This transfer in energy may be measured by either a drop in energy of the fluorescence of the first indicator molecule 320, or the detection of increased fluorescence 314 by the second indicator molecule 330.

Alternatively, the first and second fluorescent indicators may initially be positioned such that short wavelength excitation, may cause fluorescence of both the first and second fluorescent indicators, as described above. After binding of analyte 350 to the receptor, a structural change in the receptor molecule may cause the first and second fluorescent indicators to move further apart. This change in intermolecular distance may inhibit the transfer of fluorescent energy from the first indicator 320 to the second fluorescent indicator 330. This change in the transfer of energy may be measured by either a drop in energy of the fluorescence of the second indicator molecule 330, or the detection of increased fluorescence by the first indicator molecule 320.

In another embodiment, an indicator ligand may be preloaded onto the receptor. An analyte may then displace the indicator ligand to produce a change in the spectroscopic properties of the particles. In this case, the initial background absorbance is relatively large and decreases when the analyte is present. The indicator ligand, in one embodiment, has a variety of spectroscopic properties which may be measured. These spectroscopic properties include, but are not limited to, ultraviolet absorption, visible absorption, infrared absorption, fluorescence, and magnetic resonance. In one embodiment, the indicator is a dye having either a strong fluorescence, a strong ultraviolet absorption, a strong visible absorption, or a combination of these physical properties. Examples of indicators include, but are not limited to, carboxyfluorescein, ethidium bromide, 7-dimethylamino-4-methylcoumarin, 7-diethylamino-4-methylcoumarin, eosin, erythrosin, fluorescein, Oregon Green 488, pyrene, Rhodamine Red, tetramethylrhodamine, Texas Red, Methyl Violet, Crystal Violet, Ethyl Violet, Malachite green, Methyl Green, Alizarin Red S, Methyl Red, Neutral Red, o-cresolsulfonephthalein, o-cresolphthalein, phenolphthalein, Acridine Orange, B-naphthol, coumarin, and a-naphthionic acid. When the indicator is mixed with the receptor, the receptor and indicator interact with each other such that the above mentioned spectroscopic properties of the indicator, as well as other spectroscopic properties may be altered. The nature of this interaction may be a binding interaction, wherein the indicator and receptor are attracted to each other with a sufficient force to allow the newly formed receptor-indicator complex to function as a single unit. The binding of the indicator and receptor to each other may take the form of a covalent bond, an ionic bond, a hydrogen bond, a van der Waals interaction, or a combination of these bonds.

The indicator may be chosen such that the binding strength of the indicator to the receptor is less than the binding strength of the analyte to the receptor. Thus, in the presence of an analyte, the binding of the indicator with the receptor may be disrupted, releasing the indicator from the receptor. When released, the physical properties of the indicator may be altered from those it exhibited when bound to the receptor. The indicator may revert back to its original structure, thus regaining its original physical properties. For example, if a fluorescent indicator is attached to a particle that includes a receptor, the fluorescence of the particle may be strong before treatment with an analyte containing fluid. When the analyte interacts with the particle, the fluorescent indicator may be released. Release of the indicator may cause a decrease in the fluorescence of the particle, since the particle now has less indicator molecules associated with it.

Figure 9:
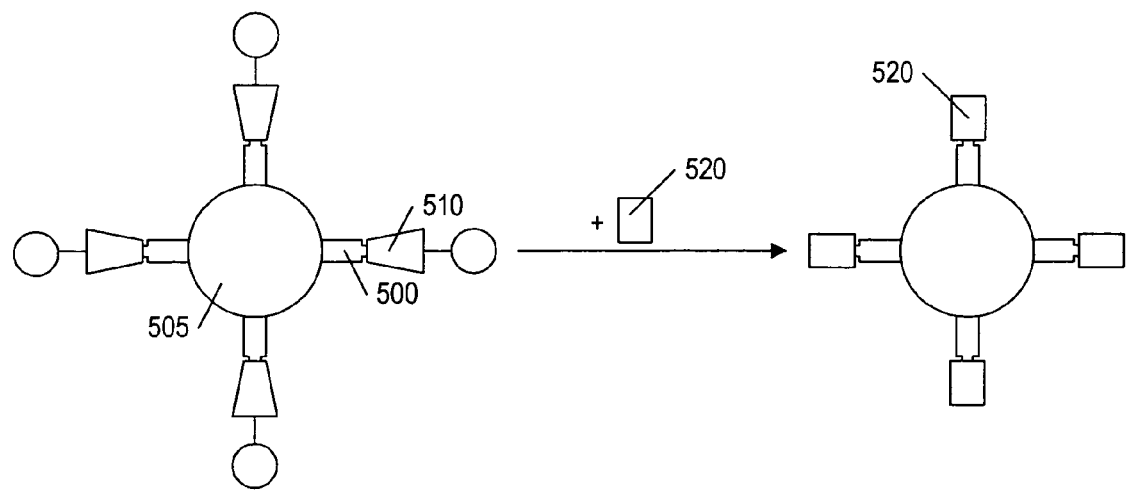
FIG. 9 depicts a schematic of the interaction of a sugar molecule with a boronic acid based receptor.
Figure 9:
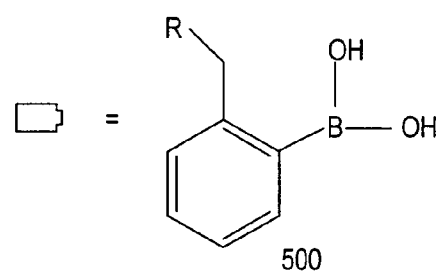
Figure 9:
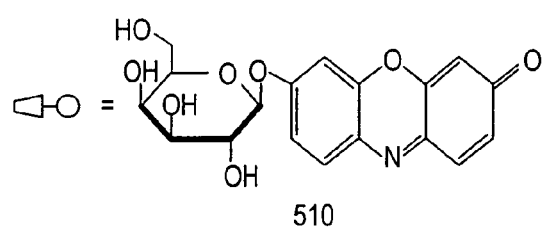
Figure 9:
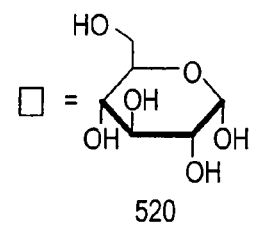

An example of this type of system is illustrated by the use of a boronic acid substituted resin 505 as a particle. Prior to testing, the boronic acid substituted resin 505 is treated with a sugar 510 which is tagged with an indicator (e.g., resorufin) as depicted in FIG. 9. The sugar 510 binds to the boronic acid receptor 500 imparting a color change to the boronic substituted resin 505 (yellow for the resorufin tagged sugar). When the boronic acid resin 505 is treated with a fluid sample which includes a sugar 520, the tagged sugar 510 may be displaced, causing a decrease in the amount of color produced by the boronic acid substituted resin 505. This decrease may be qualitatively or, with the use of a detector (e.g., a CCD detector), quantitatively monitored.

In another embodiment, a designed synthetic receptor may be used. In one embodiment, a polycarboxylic acid receptor may be attached to a polymeric resin. The polycarboxylic receptors are discussed in U.S. patent application Ser. No. 08/950,712 which is incorporated herein by reference.

In an embodiment, the analyte molecules in the fluid may be pretreated with an indicator ligand. Pretreatment may involve covalent attachment of an indicator ligand to the analyte molecule. After the indicator has been attached to the analyte, the fluid may be passed over the sensing particles. Interaction of the receptors on the sensing particles with the analytes may remove the analytes from the solution. Since the analytes include an indicator, the spectroscopic properties of the indicator may be passed onto the particle. By analyzing the physical properties of the sensing particles after passage of an analyte stream, the presence and concentration of an analyte may be determined.

For example, the analytes within a fluid may be derivatized with a fluorescent tag before introducing the stream to the particles. As analyte molecules are adsorbed by the particles, the fluorescence of the particles may increase. The presence of a fluorescent signal may be used to determine the presence of a specific analyte. Additionally, the strength of the fluorescence may be used to determine the amount of analyte within the stream.

Receptors

Figure 10:
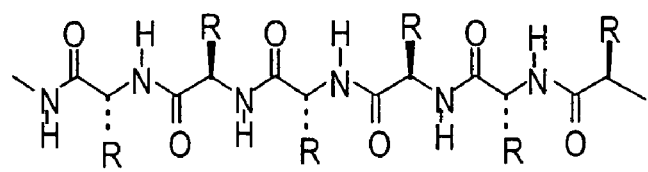
FIG. 10 depicts various synthetic receptors.
Figure 10:
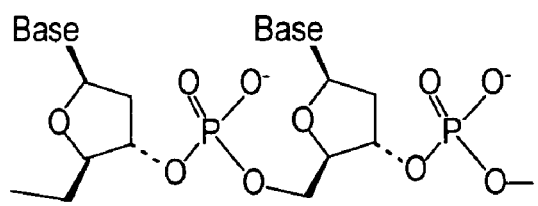
Figure 10:
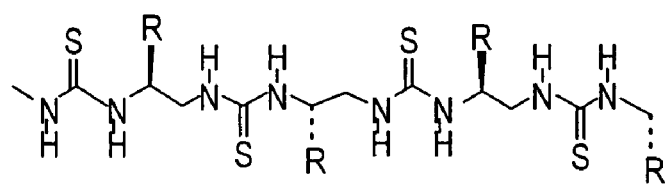
Figure 10:
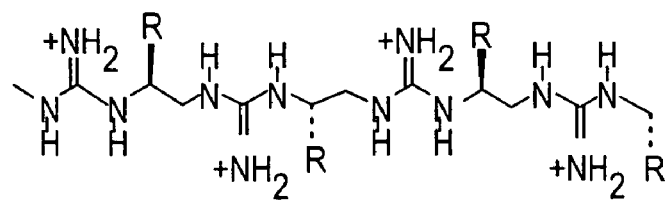

A variety of natural and synthetic receptors may be used. The synthetic receptors may come from a variety of classes including, but not limited to, polynucleotides (e.g., aptamers), peptides (e.g., enzymes and antibodies), synthetic receptors, polymeric unnatural biopolymers (e.g., polythioureas, polyguanidiniums), and imprinted polymers., some of which are generally depicted in FIG. 10. Natural based synthetic receptors include receptors which are structurally similar to naturally occurring molecules. Polynucleotides are relatively small fragments of DNA which may be derived by sequentially building the DNA sequence. Peptides may be synthesized from amino acids. Unnatural biopolymers are chemical structure which are based on natural biopolymers, but which are built from unnatural linking units. Unnatural biopolymers such as polythioureas and polyguanidiniums may be synthesized from diamines (i.e., compounds which include at least two amine functional groups). These molecules are structurally similar to naturally occurring receptors, (e.g., peptides). Some diamines may, in turn, be synthesized from amino acids. The use of amino acids as the building blocks for these compounds allow a wide variety of molecular recognition units to be devised. For example, the twenty natural amino acids have side chains that possess hydrophobic residues, cationic and anionic residues, as well as hydrogen bonding groups. These side chains may provide a good chemical match to bind a large number of targets, from small molecules to large oligosaccharides. Amino acid based peptides, polythioureas, and polyguanidiniums are depicted in FIG. 10.

Figure 11:
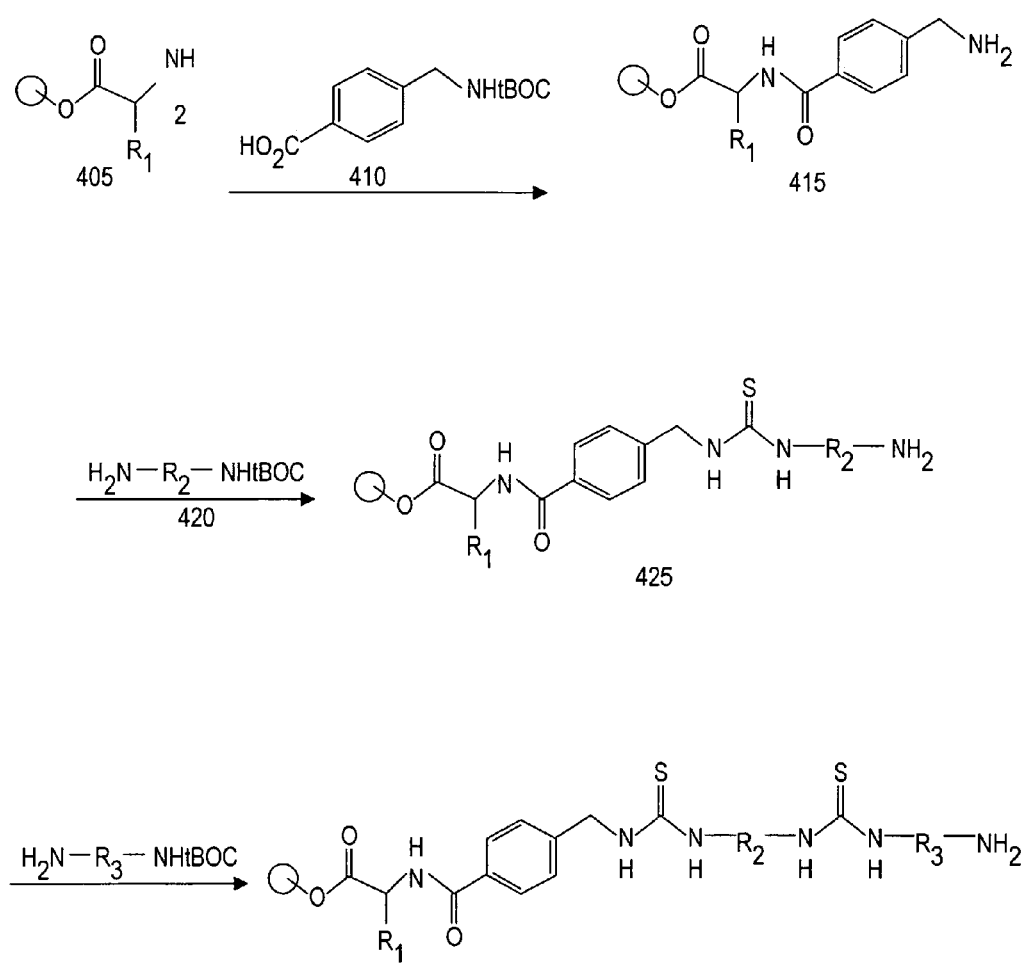
FIG. 11 depicts a synthetic pathway for the synthesis of polythioureas.

Techniques for the building of DNA fragments and polypeptide fragments on a polymer particle are well known. Techniques for the immobilization of naturally occurring antibodies and enzymes on a polymeric resin are also well known. The synthesis of polythioureas upon a resin particle may be accomplished by the synthetic pathway depicted in FIG. 11. The procedure may begin by deprotection of the terminal tBoc protecting group on an amino acid coupled to a polymeric particle. Removal of the protecting group is followed by coupling of the rigid spacer 410 to the resulting amine 405 using diisopropylcarbodiimide (DIC) and 1-hydroxybenzotriazole hydrate (HOBT). The spacer group may inhibit formation of a thiazolone by reaction of the first amino acids with subsequently formed thioureas. After the spacer group is coupled to the amino acid, another tBoc deprotection is performed to remove the spacer protecting group, giving the amine 415. At this point, monomer may be added incrementally to the growing chain, each time followed by a tBoc deprotection. The addition of a derivative of the diamine 420 (e.g., an isothiocyanate) to amine 415 gives the mono-thiourea 425. The addition of a second thiourea substituent is also depicted. After the addition of the desired number of monomers, a solution of benzylisothiocyanate or acetic anhydride may be added to cap any remaining amines on the growing oligomers. Between 1 to 20 thioureas groups may be formed to produce a synthetic polythiourea receptor.

Figure 12:
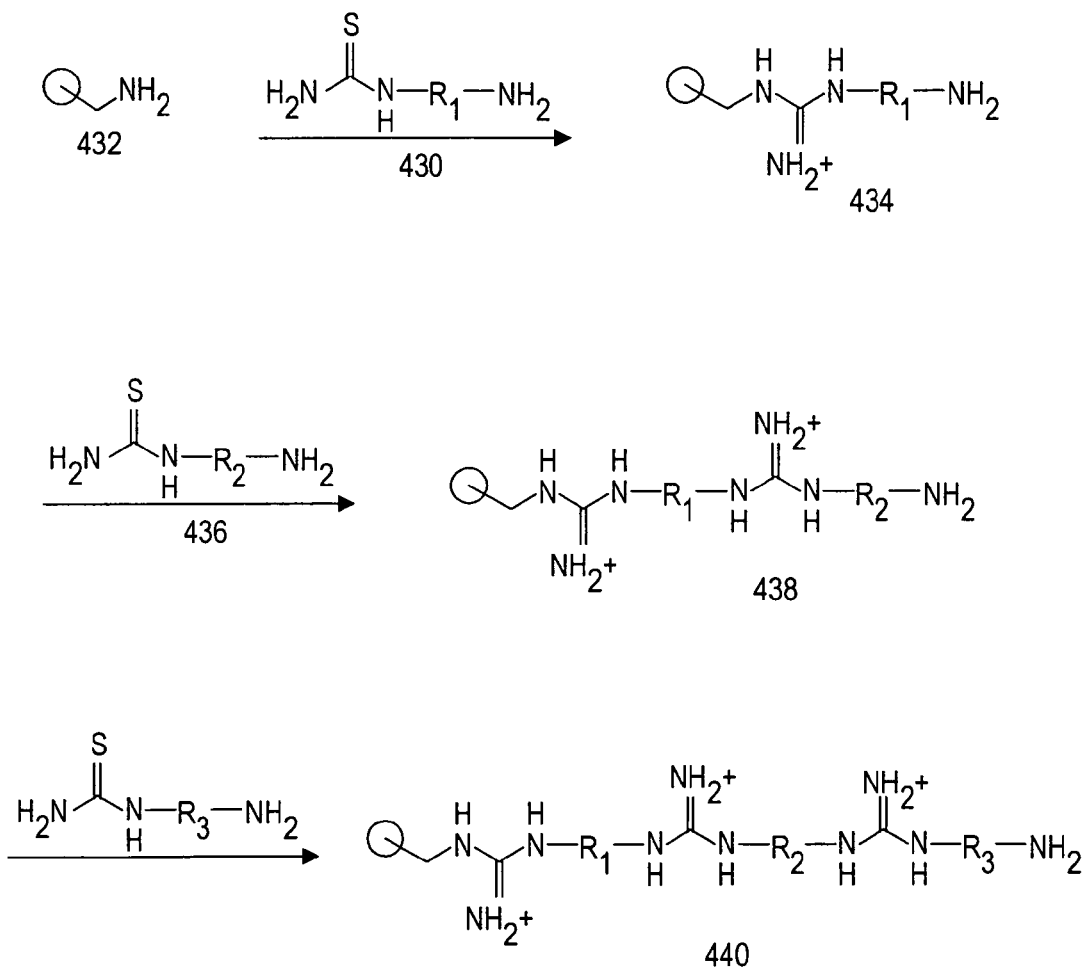
FIG. 12 depicts a synthetic pathway for the synthesis of polyguanidiniums.

The synthesis of polyguanidiniums may be accomplished as depicted in FIG. 12. In order to incorporate these guanidinium groups into the receptor, the coupling of a thiourea with a terminal amine in the presence of Mukaiyama's reagent may be utilized. The coupling of the first thiourea diamine 430 with an amino group of a polymeric particle gives the mono-guanidinium 434. Coupling of the resulting mono-guanidinium with a second thiourea diamine 436 gives a di-guanidinium 438. Further coupling may create a tri-guanidinium 440. Between 1 to 20 guanidinium groups may be formed to produce a synthetic polyguanidinium receptor.

Figure 13:
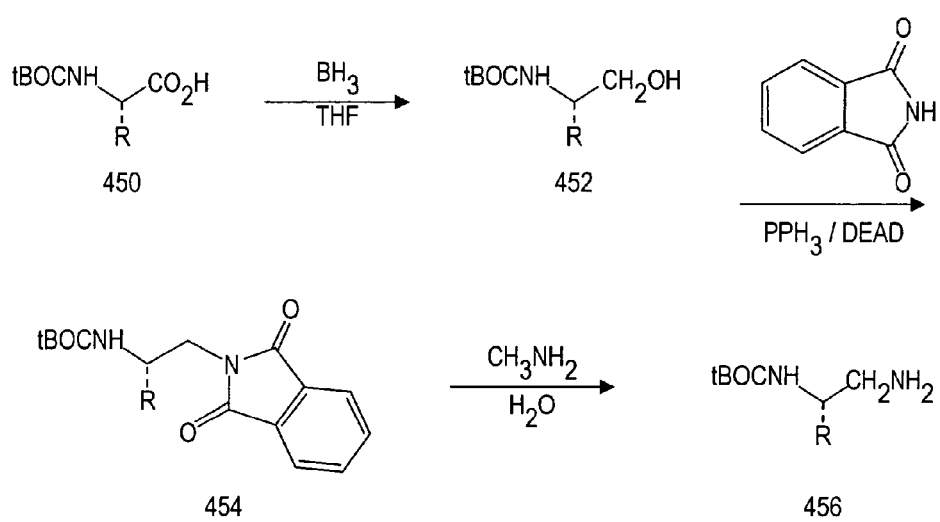
FIG. 13 depicts a synthetic pathway for the synthesis of diamines from amino acids.

The above described methods for making polythioureas and polyguanidiniums are based on the incorporation of diamines (i.e., molecules which include at least two amine functional groups) into the oligomeric receptor. The method may be general for any compound having at least two amino groups. In one embodiment, the diamine may be derived from amino acids. A method for forming diamines from amino acids is shown in FIG. 13. Treatment of a protected amino acid 450 with borane-THF reduces the carboxylic acid portion of the amino acid to the primary alcohol 452. The primary alcohol is treated with phthalimide under Mitsunobu conditions (PPh$_3$/DEAD). The resulting compound 454 is treated with aqueous methylamine to form the desired monoprotected diamine 456. The process may be accomplished such that the enantiomeric purity of the starting amino acid is maintained. Any natural or synthetic amino acid may be used in the above described method.

The three coupling strategies used to form the respective functional groups may be completely compatible with each other. The capability to mix linking groups (amides, thioureas, and guanidiniums) as well as the side chains (hydrophobic, cationic, anionic, and hydrogen bonding) may allow the creation of a diversity in the oligomers that is beyond the diversity of receptors typically found with natural biological receptors. Thus, we may produce ultra-sensitive and ultra-selective receptors which exhibit interactions for specific toxins, bacteria, and environmental chemicals. Additionally, these synthetic schemes may be used to build combinatorial libraries of particles for use in the sensor array.

In an embodiment, the indicator ligand may be incorporated into synthetic receptors during the synthesis of the receptors. The ligand may be incorporated into a monomeric unit, such as a diamine, that is used during the synthesis of the receptor. In this manner, the indicator may be covalently attached to the receptor in a controlled position. By placing the indicator within the receptor during the synthesis of the receptor, the positioning of the indicator ligand within the receptor may be controlled. This control may be difficult to achieve after synthesis of the receptor is completed.

Figure 14:
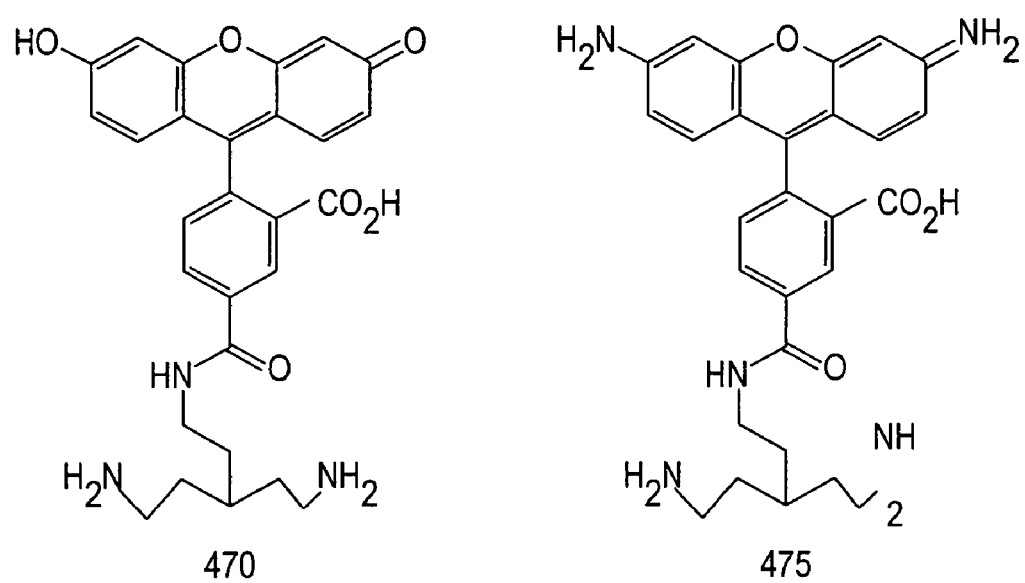
FIG. 14 depicts fluorescent diamino monomers.

In one embodiment, a fluorescent group may be incorporated into a diamine monomer for use in the synthetic sequences. Examples of monomeric units which may be used for the synthesis of a receptor are depicted in FIG. 14. The depicted monomers include fluorescent indicator groups. After synthesis, the interaction of the receptor with the analyte may induce changes in the spectroscopic properties of the molecule. Typically, hydrogen bonding or ionic substituents on the fluorescent monomer involved in analyte binding have the capacity to change the electron density and/or rigidity of the fluorescent ring system, thereby causing observable changes in the spectroscopic properties of the indicator. For fluorescent indicators such changes may be exhibited as changes in the fluorescence quantum yield, maximum excitation wavelength, and/or maximum emission wavelength. This approach does not require the dissociation of a preloaded fluorescent ligand, which may be limited in response time by $k_{(off)}$). While fluorescent ligands are shown here, it is to be understood that a variety of other ligand may be used including calorimetric ligands.

In another embodiment, two fluorescent monomers for signaling may be used for the synthesis of the receptor. For example, compound 470 (a derivative of fluorescein) and compound 475 (a derivative of rhodamine), depicted in FIG. 14, may both be incorporated into a synthetic receptor. Compound 470 contains a common colorimetric/fluorescent probe that will, in some embodiments, send out a modulated signal upon analyte binding. The modulation may be due to resonance energy transfer to compound 475. When an analyte binds to the receptor, structural changes in the receptor may alter the distance between monomeric units 470 and 475. It is well known that excitation of fluorescein can result in emission from rhodamine when these molecules are oriented correctly. The efficiency of resonance energy transfer from monomers 470 to 475 will depend strongly upon the presence of analyte binding; thus, measurement of rhodamine fluorescence intensity (at a substantially longer wavelength than fluorescein fluorescence) may serve as an indicator of analyte binding. To greatly improve the likelihood of a modulatory fluorescein-rhodamine interaction, multiple rhodamine tags may be attached at different sites along a receptor molecule without substantially increasing background rhodamine fluorescence (only rhodamine very close to fluorescein will yield appreciable signal). This methodology may be applied to a number of alternate fluorescent pairs.

In an embodiment, a large number of chemical/biological agents of interest to the military and civilian communities may be sensed readily by the described array sensors including both small and medium size molecules. For example, it is known that nerve gases typically produce phosphate structures upon hydrolysis in water. The presence of molecules which contain phosphate functional groups may be detected using polyguanidiniums. Nerve gases which have contaminated water sources may be detected by the use of the polyguanidinium receptors described above.

In order to identify, sense, and quantitate the presence of various bacteria using the proposed micro-machined sensor, two strategies may be used. First, small molecule recognition and detection may be exploited. Since each bacteria possesses a unique and distinctive concentration of the various cellular molecules, such as DNA, proteins, metabolites, and sugars, the fingerprint (i.e., the concentration and types of DNA, proteins, metabolites, and sugars) of each organism is expected to be unique. Hence, the analytes obtained from whole bacteria or broken down bacteria may be used to determine the presence of specific bacteria. A series of receptors specific for DNA molecules, proteins, metabolites, and sugars may be incorporated into an array. A solution containing bacteria, or more preferably broken down bacteria, may be passed over the array of particles. The individual cellular components of the bacteria may interact in a different manner with each of the particles. This interaction will provide a pattern within the array which may be unique for the individual bacteria. In this manner, the presence of bacteria within a fluid may be determined.

In another embodiment, bacteria may be detected as whole entities, as found in ground water, aerosols, or blood. To detect, sense, and identify intact bacteria, the cell surface of one bacteria may be differentiated from other bacteria. One method of accomplishing this differentiation is to target cell surface oligosaccharides (i.e. sugar residues). Each bacterial class (gram negative, gram positive, etc.) displays a different oligosaccharide on their cell surfaces. The oligosaccharide, which is the code that is read by other cells giving an identification of the cell, is part of the cell-cell recognition and communication process. The use of synthetic receptors which are specific for oligosaccharides may be used to determine the presence of specific bacteria by analyzing for the cell surface oligosaccharides.

In another embodiment, the sensor array may be used to optimize which receptor molecules should be used for a specific analyte. An array of receptors may be placed within the cavities of the supporting member and a stream containing an analyte may be passed over the array. The reaction of each portion of the sensing array to the known analyte may be analyzed and the optimal receptor determined by determining which particle, and therefore which receptor, exhibits the strongest reaction toward the analyte. In this manner, a large number of potential receptors may be rapidly scanned. The optimal receptor may then be incorporated into a system used for the detection of the specific analyte in a mixture of analytes.

It should be emphasized that although some particles may be purposefully designed to bind to important species (biological agents, toxins, nerve gasses, etc.), most structures will possess nonspecific receptor groups. One of the advantages associated with the proposed sensor array is the capacity to standardize each array of particles via exposure to various analytes, followed by storage of the patterns which arise from interaction of the analytes with the particles. Therefore, there may not be a need to know the identity of the actual receptor on each particle. Only the characteristic pattern for each array of particles is important. In fact, for many applications it may be less time consuming to place the various particles into their respective holders without taking precautions to characterize the location associated with the specific particles. When used in this manner, each individual sensor array may require standardization for the type of analyte to be studied.

On-site calibration for new or unknown toxins may also be possible with this type of array. Upon complexation of an analyte, the local microenvironment of each indicator may change, resulting in a modulation of the light absorption and/or emission properties. The use of standard pattern recognition algorithms completed on a computer platform may serves as the intelligence factor for the analysis. The "fingerprint" like response evoked from the simultaneous interactions occurring at multiple sites within the substrate may be used to identify the species present in unknown samples.

The above described sensor array system offers a number of distinct advantages over exiting technologies. One advantage is that "real time" detection of analytes may be performed. Another advantage is that the simultaneous detection of multiple analytes may be realized. Yet another advantage is that the sensor array system allows the use of synthetic reagents as well as biologically produced reagents. Synthetic reagents typically have superior sensitivity and specificity toward analytes when compared to the biological reagents. Yet another advantage is that the sensor array system may be readily modified by simply changing the particles which are placed within the sensor array. This interchangability may also reduce production costs.

EXAMPLES

1. The Determination of pH Using a Chemically Sensitive Particle.

Figure 15:
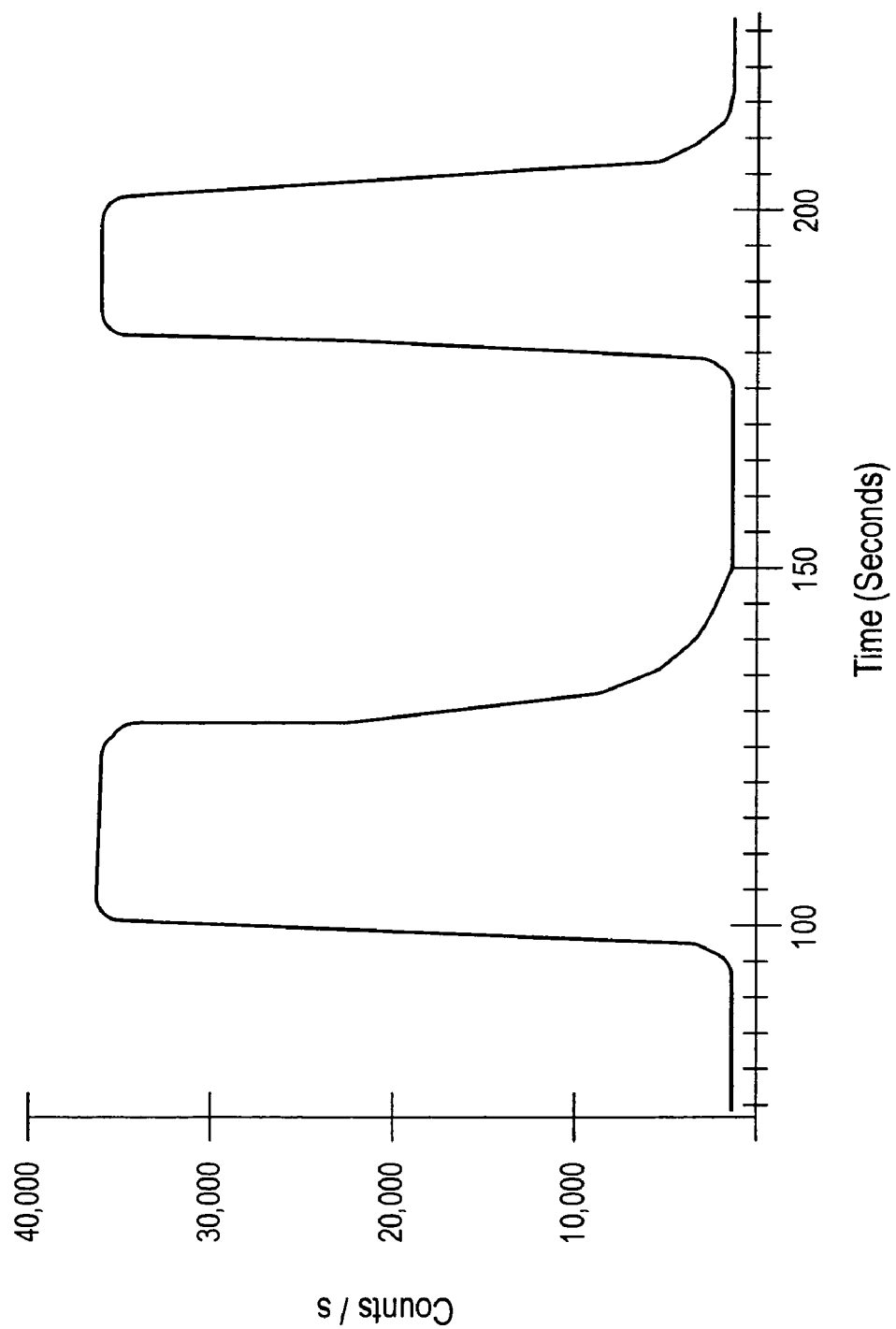
FIG. 15 depicts a plot of counts/sec. (i.e., intensity) vs. time as the pH of a solution surrounding a particle coupled to o-cresolphthalein is cycled from acidic to basic conditions.

Shown in FIG. 15 is the magnitude of the optical signal transmitted through a single polymer particle derivatized with o-cresolphthalein. Here, a filter is used to focus the analysis on those wavelengths which the dye absorbs most strongly (i.e., about 550 nm). Data is provided for the particle as the pH is cycled between acid and basic environments. In acidic media (i.e., at times of 100-150 seconds and 180-210 seconds), the particle is clear and the system yields large signals (up to greater than 300,000 counts) at the optical detector. Between times of 0-100 and 150-180 seconds, the solution was made basic. Upon raising the pH (i.e., making the solution more basic), the particle turns purple in color and the transmitted green light is greatly diminished. Large signal reductions are recorded under such circumstances. The evolution of the signal changes show that the response time is quite rapid, on the order of 10 seconds. Furthermore, the behavior is highly reproducible.

2. The Simultaneous Detection of $Ca^{+2}$, $Ce^{+3}$, and pH by a Sensor Array System.

The synthesis of four different particles was accomplished by coupling a variety of indictor ligands to a polyethylene glycol-polystyrene ("PEG-PS") resin particle. The PEG-PS resin particles were obtained from Novabiochem Corp., La Jolla, Calif. The particles have an average diameter of about 130 µm when dry and about 250 µm when wet. The indicator ligands of fluorescein, o-cresolphthalein complexone, and alizarin complexone were each attached to PEG-PS resin particles using a dicyclohexylcarbodiimide (DCC) coupling between a terminal resin bound amine and a carboxylic acid on the indicator ligand.

Figure 16:
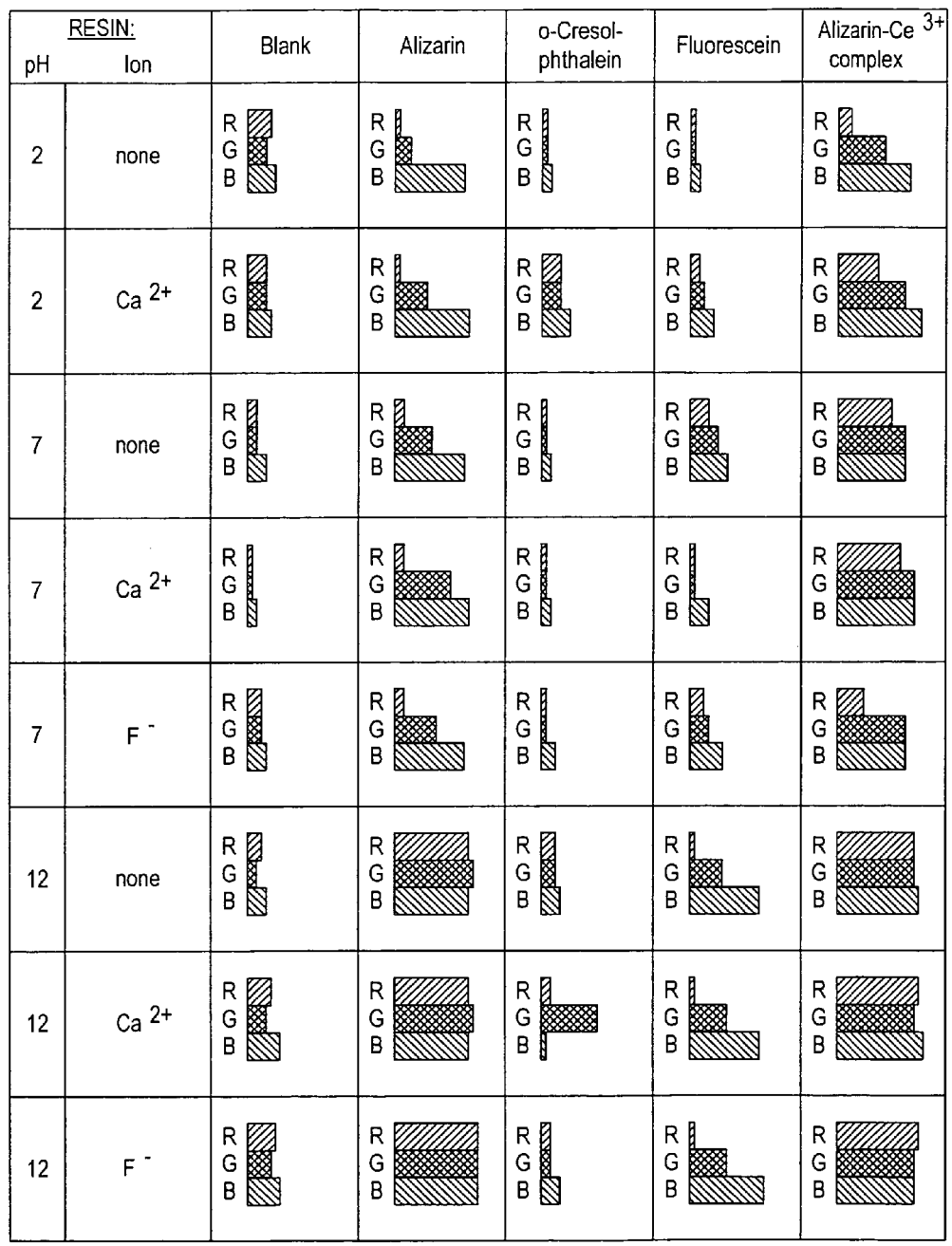
FIG. 16 depicts the color responses of a variety of sensing particles to solutions of $Ca^{+2}$ and various pH levels.

These synthetic receptors, localized on the PEG-PS resin to create sensing particles, were positioned within micromachined wells formed in silicon/silicon nitride wafers, thus confining the particles to individually addressable positions on a multicomponent chip. These wells were sized to hold the particles in both swollen and unswollen states. Rapid introduction of the test fluids can be accomplished using these structures while allowing spectrophotometric assays to probe for the presence of analytes. For the identification and quantification of analyte species, changes in the light absorption and light emission properties of the immobilized resin particles can be exploited, although only identification based upon absorption properties are discussed here. Upon exposure to analytes, color changes for the particles were found to be 90% complete within one minute of exposure, although typically only seconds were required. To make the analysis of the colorimetric changes efficient, rapid, and sensitive, a charge-coupled-device (CCD) was directly interfaced with the sensor array. Thus, data streams composed of red, green, and blue (RGB) light intensities were acquired and processed for each of the individual particle elements. The red, blue, and green responses of the particles to various solutions are graphically depicted in FIG. 16.

The true power of the described bead sensor array occurs when simultaneous evaluation of multiple chemically distinct bead structures is completed. A demonstration of the capacity of five different beads is provided in FIG. 16. In this case, blank, alizarin, o-cresol phthalein, fluorescein, and alizarin-Ce3+ complex derivatized beads serve as a matrix for subtle differentiation of chemical environments. The blank bead is simply a polystyrene sphere with no chemical derivatization. The bead derivatized with o-cresolphthalein responds to Ca+2 at pHs values around 10.0. The binding of calcium is noted from the large green color attenuation noted for this dye while exposed to the cation. Similarly, the fluorescein derivatized bead acts as a pH sensor. At pHs below 7.4 it is light yellow, but at higher pHs it turns dark orange. Interesting, the alizarin complexone plays three distinct roles. First, it acts as a proton sensor yielding a yellow color at pHs below 4.5, orange is noted at pHs between 4.5 and 11.5, and at pHs above 11.5 a blue hue is observed. Second, it functions as a sensor for lanthanum ions at lower pHs by turning yellow to orange. Third, the combination of both fluoride and lanthanum ions results in yellow/orange coloration.

The analysis of solutions containing various amount of $Ca^{+2}$ or $F^-$ at various pH levels was performed using alizarin complexone, o-cresolphthalein complexone, 5-carboxy fluorescein, and alizarin-$Ce^{3+}$ complex. A blank particle in which the terminal amines of a PEG-PS resin particle have been acylated was also used. In this example, the presence of $Ca^{+2}$ (0.1 M $Ca(NO_3)_2$) was analyzed under conditions of varying pH. The pH was varied to values of 2, 7, and 12, all buffered by a mixture of 0.04 M phosphate, 0.04 M acetate, and 0.04 M borate. The RGB patterns for each sensor element in all environments were measured. The bead derivatized with o-cresolphthalein responds to $Ca^{+2}$ at pH values around 12. Similarly, the 5-carboxy fluorescein derivatized bead acts as a pH sensor. At pHs below 7.4 it is light yellow, but at higher pHs it turns dark orange. Interesting, the alizarin complexone plays three distinct roles. First, it acts as a proton sensor yielding a yellow color at pHs below 4.5, orange is noted at pHs between 4.5 and 11.5, and at pHs above 11.5 a blue hue is observed. Second, it functions as a sensor for lanthanum ions at lower pHs by turning yellow to orange. Third, the combination of both fluoride and lanthanum ions results in yellow/orange coloration.

This example demonstrates a number of important factors related to the design, testing, and functionality of micromachined array sensors for solution analyses. First, derivatization of polymer particles with both colorimetric and fluorescent dyes was completed. These structures were shown to respond to pH and $Ca^{2+}$. Second, response times well under 1 minute were found. Third, micromachined arrays suitable both for confinement of particles, as well as optical characterization of the particles, have been prepared. Fourth, integration of the test bed arrays with commercially available CCD detectors has been accomplished. Finally, simultaneous detection of several analytes in a mixture was made possible by analysis of the RGB color patterns created by the sensor array.

3. The Detection of Sugar Molecules Using a Boronic Acid Based Receptor.

A series of receptors were prepared with functionalities that associate strongly with sugar molecules, as depicted in FIG. 9. In this case, a boronic acid sugar receptor 500 was utilized to demonstrate the functionality of a new type of sensing scheme in which competitive displacement of a resorufin derivatized galactose sugar molecule was used to assess the presence (or lack thereof) of other sugar molecules. The boronic acid receptor 500 was formed via a substitution reaction of a benzylic bromide. The boronic acid receptor was attached to a polyethylene glycol-polystyrene ("PEG-PS") resin particle at the "R" position. Initially, the boronic acid derivatized particle was loaded with resorufin derivatized galactose 510. Upon exposure of the particle to a solution containing glucose 520, the resorufin derivatized galactose molecules 510 are displaced from the particle receptor sites. Visual inspection of the optical photographs taken before and after exposure to the sugar solution show that the boron substituted resin is capable of sequestering sugar molecules from an aqueous solution. Moreover, the subsequent exposure of the colored particles to a solution of a non-tagged sugar (e.g., glucose) leads to a displacement of the bound colored sugar reporter molecule. Displacement of this molecule leads to a change in the color of the particle. The sugar sensor turns from dark orange to yellow in solutions containing glucose. The particles were also tested in conditions of varying pH. It was noted that the color of the particles changes from dark orange to yellow as the pH is varied from low pH to high pH.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A sensor array for detecting multiple analytes in a fluid comprising:

a supporting member, wherein a plurality of cavities are formed within the supporting member and the cavities extend through the supporting member;

a plurality of particles positioned within the plurality of cavities, wherein the particles are configured to produce a signal when the particle interacts with an analyte;

a cover positioned above the supporting member and configured to inhibit dislodgment of the particle during use; and one or more support structures coupled to the supporting member and to the cover;

wherein the one or more support structures space the cover apart from the supporting member by a fixed distance to define a channel therebetween, and wherein the fluid enters the cavity via the channel during use.

2. The sensor array of claim 1, wherein the particle is composed of a polymeric resin, and further comprising a receptor molecule coupled to the polymeric resin.

3. The sensor array of claim 1, wherein the particle has a size ranging from about 0.05 microns to about 500 microns in diameter.

4. The sensor array of claim 1, wherein the particle has a size ranging from about 0.05 microns to bout 500 microns in diameter, and wherein the cavity is configured to substantially contain the particle.

5. The sensor array of claim 1, wherein the supporting member comprises a plastic material.

6. The sensor array of claim 1, wherein the supporting member comprises a silicon wafer.

7. The sensor array of claim 6, wherein the cavities are substantially pyramidal in shape and wherein the sidewalls of the cavities are substantially tapered at an angle from about 50 degrees to about 60 degrees.

8. The sensor array of claim 1, further comprising channels in the supporting member, wherein the channels are configured to allow the fluid to flow through the channels into and away from the cavities.

9. The sensor array of claim 1, further comprising an inner surface coating wherein the inner surface coating is configured to inhibit dislodgment of the particle.

10. The sensor array of claim 1, further comprising a detector coupled to the bottom surface of the supporting member, wherein the detector is positioned below the cavities.

11. The sensor array of claim 1, wherein the cover is substantially transparent.

12. The sensor array of claim 11, wherein the cover comprises plastic, glass, quartz, silicon oxide, or silicon nitride.

13. The sensor array of claim 1, wherein at least one of the support structures comprises a polymer material or a silicon-based material.

* * * * *

UNITED STATES PATENT AND TRADEMARK OFFICE
CERTIFICATE OF CORRECTION

| | | |
|---|---|---|
| PATENT NO. | : 7,491,552 B2 | Page 1 of 1 |
| APPLICATION NO. | : 11/039054 | |
| DATED | : February 17, 2009 | |
| INVENTOR(S) | : John T. McDevitt et al. | |

It is certified that error appears in the above-identified patent and that said Letters Patent is hereby corrected as shown below:

On the Title page, item (*) Notice, line 4, insert --This patent is subject to a terminal disclaimer.--.

Signed and Sealed this

Twenty-eighth Day of April, 2009

JOHN DOLL
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 7,491,552 B2 | Page 1 of 1 |
| APPLICATION NO. | : 11/039054 | |
| DATED | : February 17, 2009 | |
| INVENTOR(S) | : John T. McDevitt et al. | |

It is certified that error appears in the above-identified patent and that said Letters Patent is hereby corrected as shown below:

In the Specification

In column 1, lines 16-20, delete the entire contents of lines 16-20 and insert --This invention was made with government support under Grant no. DK051818 and DK057306 awarded by the National Institutes of Health; and Grant no. 9631394 awarded by the National Science Foundation; and Grant no. N00014-94-1-0706 awarded by the Office of Naval Research. The government has certain rights in the invention.-- therefor.

Signed and Sealed this
Ninth Day of June, 2015

Michelle K. Lee
*Director of the United States Patent and Trademark Office*